(12) United States Patent
Kemp et al.

(10) Patent No.: US 10,590,075 B2
(45) Date of Patent: Mar. 17, 2020

(54) CYANOPYRROLIDINE DERIVATIVES AS INHIBITORS FOR DUBS

(71) Applicant: Mission Therapeutics Limited, Cambridge (GB)

(72) Inventors: Mark Ian Kemp, Cambridge (GB); Michael David Woodrow, Cambridge (GB)

(73) Assignee: MISSION THERAPEUTICS LIMITED, Cambridge (GB)

( * ) Notice: Subject to any disclaimer, the term of this patent is extended or adjusted under 35 U.S.C. 154(b) by 0 days.

(21) Appl. No.: 16/060,299

(22) PCT Filed: Dec. 21, 2016

(86) PCT No.: PCT/GB2016/054022
§ 371 (c)(1),
(2) Date: Jun. 7, 2018

(87) PCT Pub. No.: WO2017/109488
PCT Pub. Date: Jun. 29, 2017

(65) Prior Publication Data
US 2018/0362460 A1  Dec. 20, 2018

(30) Foreign Application Priority Data
Dec. 23, 2015 (GB) .................. 1522768.9

(51) Int. Cl.
| | | |
|---|---|---|
| C07D 207/16 | (2006.01) |
| A61K 31/4025 | (2006.01) |
| C07D 403/12 | (2006.01) |
| C07D 413/14 | (2006.01) |
| C07D 413/12 | (2006.01) |
| C07D 417/12 | (2006.01) |
| C07D 417/14 | (2006.01) |
| C07D 207/10 | (2006.01) |
| A61P 35/00 | (2006.01) |
| C07D 401/12 | (2006.01) |

(52) U.S. Cl.
CPC .......... *C07D 207/16* (2013.01); *A61P 35/00* (2018.01); *C07D 207/10* (2013.01); *C07D 401/12* (2013.01); *C07D 403/12* (2013.01); *C07D 413/12* (2013.01); *C07D 413/14* (2013.01); *C07D 417/12* (2013.01); *C07D 417/14* (2013.01)

(58) Field of Classification Search
CPC ................. C07D 207/16; A61K 31/4025
See application file for complete search history.

(56) References Cited

U.S. PATENT DOCUMENTS

2019/0055232 A1* 2/2019 Gibson ............... C07D 401/14

FOREIGN PATENT DOCUMENTS

| WO | 0177073 A1 | 10/2001 |
|---|---|---|
| WO | 2013058691 A1 | 4/2013 |
| WO | 2015054555 A1 | 4/2015 |
| WO | 2015179190 A1 | 11/2015 |
| WO | 2016/046530 A1 | 3/2016 |
| WO | 2016156816 A1 | 10/2016 |
| WO | 2017/009650 A1 | 1/2017 |
| WO | 2017/093718 A1 | 6/2017 |
| WO | 2017/109488 A1 | 6/2017 |
| WO | 2017103614 A1 | 6/2017 |
| WO | 2017/141036 A1 | 8/2017 |
| WO | 2017/149313 A1 | 9/2017 |
| WO | 2017/158381 A1 | 9/2017 |
| WO | 2017/158388 A1 | 9/2017 |
| WO | 2017/163078 A1 | 9/2017 |
| WO | 2018060689 A1 | 4/2018 |
| WO | 2018060691 A1 | 4/2018 |
| WO | 2018060742 A1 | 4/2018 |

(Continued)

OTHER PUBLICATIONS

Patani, Bioisosterism: A Rational Approach in Drug Design, Chemical Review, vol. 96, No. 8, p. 3147-3176 (Year: 1996).*
Ward et al., "Quantitative Chemical Proteomic Profiling of Ubiquitin Specific Proteases in Intact Cancer Cells," ACS Chem. Biol. 2016, 11, 3268-3272.
The International Search Report and Written Opinion, dated Mar. 9, 2017, in the corresponding PCT Appl. No. PCT/GB2016/054022.
Falgueyret et al., "Novel, Nonpeptidic Cyanamides as Potent and Reversible Inhibitors of Human Cathepsins K and L," J. Med. Chem. 2001, 44, 94-104.
Laine et al., "Discovery of Novel Cyanamide-Based Inhibitors of Cathepsin C," ACS Med. Chem. Lett. 2011, 2, 142-147.

(Continued)

*Primary Examiner* — Karen Cheng

(57) ABSTRACT

The present invention relates to novel compounds and methods for the manufacture of inhibitors of deubiquitylating enzymes (DUBs). In particular, the invention relates to the inhibition of Cezanne 1 and ubiquitin C-terminal hydrolase 30 or Ubiquitin Specific Peptidase 30 (USP30). The invention further relates to the use of DUB inhibitors in the treatment of cancer. Compounds of the invention include compounds having the formula (I): pharmaceutically acceptable salt thereof, wherein $R^{1a}$, $R^{1b}$, $R^{1c}$, $R^{1d}$, $R^{1e}$, $R^{1f}$ and A are as defined herein.

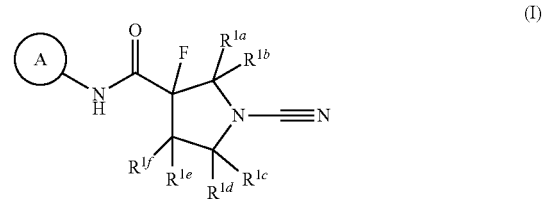

(I)

18 Claims, 1 Drawing Sheet

(56) References Cited

FOREIGN PATENT DOCUMENTS

WO      2018065768 A1    4/2018

OTHER PUBLICATIONS

Pareja et al, "Deubiquitination of EGFR by Cezanne-1 contributes to cancer progression", Oncogene. Oct. 25, 2012; 31(43): 4599-4608.
Rydzewski et al, "Peptidic 1-Cyanopyrrolidines: Synthesis and SAR of a Series of Potent, Selective Cathepsin Inhibitors", Bioorganic & Medicinal Chemistry 10 (2002) 3277-3284.
Deaton et al, "Novel and potent cyclic cyanamide-based cathepsin K inhibitors", Bioorganic & Medicinal Chemistry Letters 15 (2005) 1815-1819.
Oballa et al, "A generally applicable method for assessing the electrophilicity and reactivity of diverse nitrile-containing compounds", Bioorganic & Medicinal Chemistry Letters 17 (2007) 998-1002.
Zapf et al, "Covalent Inhibitors of Interleukin-2 Inducible T Cell Kinase (Itk) with Nanomolar Potency in a Whole-Blood Assay", J. Med. Chem. 2012, 55, 10047-10063.

\* cited by examiner

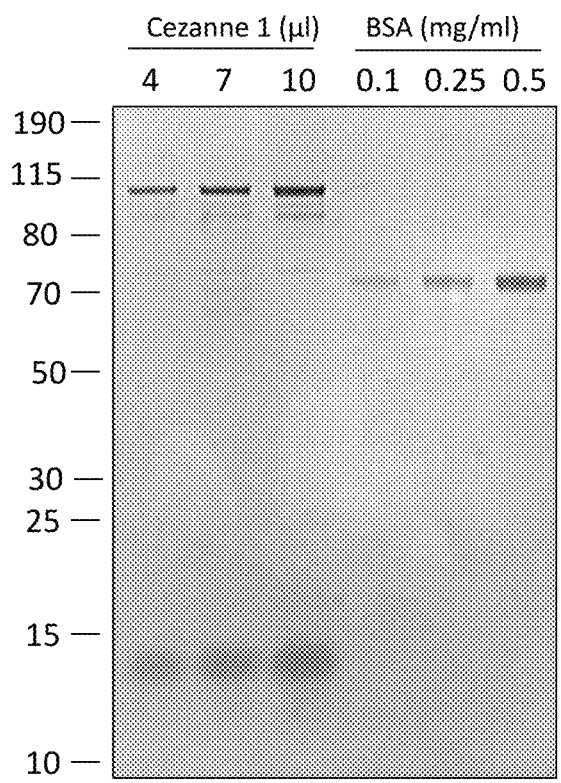
Figure 1: Expression and purification of FLAG-Cezanne 1 from mammalian cells
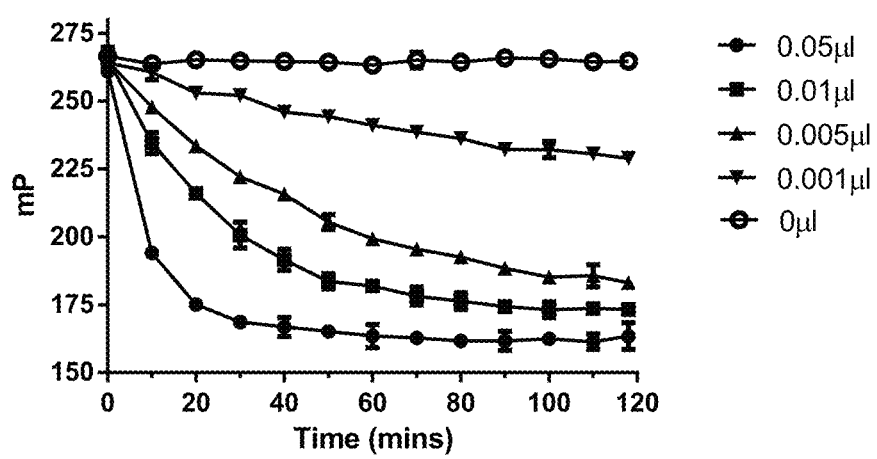
Figure 2: Cezanne 1 kinetic assay for high throughput screening of compounds using an isopeptide linked substrate

CYANOPYRROLIDINE DERIVATIVES AS INHIBITORS FOR DUBS

CROSS-REFERENCE TO RELATED APPLICATIONS

This application is a National Stage Application of PCT/GB2016/054022 filed Dec. 21, 2016, which claims priority from UK Patent Application No. 1522768.9, filed on Dec. 23, 2015. The priority of said PCT and UK Patent Application are claimed. Each of the prior mentioned applications is hereby incorporated by reference herein in its entirety.

The present invention relates to novel compounds and methods for the manufacture of inhibitors of deubiquitylating enzymes (DUBs). In particular, the invention relates to the inhibition of Cezanne 1. The invention further relates to the use of DUB inhibitors in the treatment of cancer.

BACKGROUND TO THE INVENTION

The listing or discussion of an apparently prior-published document in this specification should not necessarily be taken as an acknowledgement that the document is part of the state of the art or is common general knowledge.

Ubiquitin is a small protein consisting of 76 amino acids that is important for the regulation of protein function in the cell. Ubiquitylation and deubiquitylation are enzymatically mediated processes by which ubiquitin is covalently bound or cleaved from a target protein. These processes have been implicated in the regulation of many cellular functions including cell cycle progression, apoptosis, modification of cell surface receptors, regulation of DNA transcription and DNA repair. Thus, the ubiquitin system has been implicated in the pathogenesis of numerous disease states including inflammation, viral infection, metabolic dysfunction, CNS disorders, and oncogenesis.

Ubiquitin molecules are cleaved from proteins by deubiquitylating enzymes (DUBs), of which there are approximately 95 DUBs in human cells, divided into sub-families based on sequence homology. The ovarian tumour (OTU) family consists of at least 14 active DUBs and are characterised by the presence of an OTU domain and the tendency to cleave ubiquitin chains in a linkage specific manner. Cezanne 1, also known as OTUD7B, is an 843 amino acid protein that was identified owing to its similarity to the OTU family member A20 that has been shown biochemically to have a strong preference for K11 ubiquitin chain linkages.

Cezanne 1 has been shown to act as a negative regulator of both the canonical and the non-canonical NF-κB pathway. It has been shown that Cezanne 1 acts on the canonical pathway by processing K63 chains on the RIP 1 protein and on the non-canonical pathway by deubiquitylation of the inhibitory component TRAF3 (TNF receptor associated factor 3). It has also been shown to have a role in hypoxia by regulating HIF1α (hypoxia inducible factor 1α) protein levels. Cezanne 1 siRNA decreased HIF1α protein levels under hypoxia, and accordingly decreased HIF1α target gene expression. Knockdown of Cezanne 1 led to higher levels of apoptosis following hypoxia. Since HIF1α has oncogenic properties, and Cezanne 1 has a pro-survival role in hypoxia, Cezanne 1 has been suggested to be a good target for pharmacological intervention.

Cezanne 1 has been shown to have a role in cell proliferation, migration and invasion by antagonizing EGFR (epidermal growth factor receptor) internalisation and degradation. Cezanne 1 and Cezanne 2 were identified in a genetic screen to find a DUB enzyme for EGFR. Cezanne 1 overexpression led to higher levels of phosphorylated EGFR, lower levels of ubiquitylated EGFR and EGFR stabilization. In MDA-MB-231 breast cancer cells, knockdown of Cezanne 1 led to decreased invasion and migration. Analysis of The Cancer Genome Atlas by Pareja et al., showed that Cezanne 1 was overexpressed in breast cancer and amplification of the gene was seen in a third of breast tumours. The level of Cezanne 1 expression correlated with poor prognosis.

Although there has been a handful of DUB inhibitors published in the literature, there is a continuing need for compounds and pharmaceutical compositions which inhibit DUBs such as Cezanne 1 and USP30 for the treatment of cancer and other indications where DUB activity is observed.

SUMMARY OF THE INVENTION

In accordance with a first aspect of the invention there is provided a compound of formula (I)

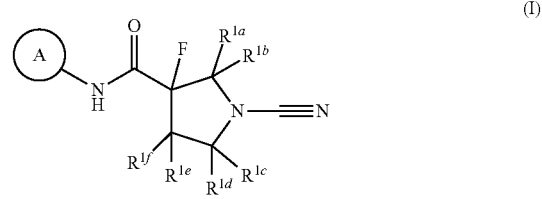

or a pharmaceutically acceptable salt thereof, wherein:
$R^{1a}$, $R^{1b}$, $R^{1c}$ and $R^{1d}$ each independently represent hydrogen or an optionally substituted $C_1$-$C_6$ alkyl, or $R^{1a}$ is linked to $R^{1b}$ to form an optionally substituted cycloalkyl ring, or $R^{1d}$ is linked to $R^{1c}$ or $R^{1e}$ to form an optionally substituted cycloalkyl ring;

$R^{1e}$ and $R^{1f}$ each independently represent hydrogen, fluorine, cyano, hydroxyl, amino, optionally substituted $C_1$-$C_6$ alkyl, optionally substituted $C_1$-$C_6$ alkoxy or an optionally substituted 5 or 6 membered aryl or heteroaryl ring, or $R^{1e}$ and $R^{1f}$ together form an optionally substituted cycloalkyl ring, or $R^{1e}$ is linked to $R^{1d}$ to form an optionally substituted cycloalkyl ring;

A is an optionally substituted 5 to 10 membered heteroaryl or aryl ring.

A may represent a 5 to 10 membered heteroaryl or aryl ring substituted with one or more of $Q^1$-$(R^2)_n$, wherein:
n is 0 or 1;

$Q^1$ represents halogen, cyano, oxo, nitro, —$OR^3$, —$SR^3$, —$NR^3R^4$, —$CONR^3R^4$, —$NR^3COR^4$, —$NR^3 CONR^4R^5$, —$COR^3$, —$C(O)OR^3$, —$SO_2R^3$, —$SO_2NR^3R^4$, —$NR^3SO_2R^4$, —$NR^3SO_2NR^4R^5$, —$NR^3C(O)OR^4$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, a covalent bond, an oxygen atom, a sulphur atom, —SO—, —$SO_2$—, —CO—, —C(O)O—, —$CONR^3$—, —$NR^3$—, —$NR^3CO$—, —$NR^3CONR^4$—, —$SO_2NR^3$—, —$NR^3SO_2$—, —$NR^3SO_2NR^4$—, —$NR^3C(O)O$—, —$NR^3C(O)OR^4$—, optionally substituted $C_1$-$C_6$ alkylene or optionally substituted —$C_2$-$C_6$ alkenylene;

$R^3$, $R^4$ and $R^5$ each independently represent hydrogen, optionally substituted $C_1$-$C_6$ alkyl or optionally substituted $C_1$-$C_6$ alkylene.

When n is 1, $R^2$ represents an optionally substituted 3 to 10 membered heterocyclyl, heteroaryl, aryl or cycloalkyl ring. (When n is 0, $Q_1$ is present and $R^2$ is absent).

$R^2$ may be optionally substituted with one or more substituents selected from halogen, cyano, oxo, nitro, —$OR^6$, —$SR^6$, —$NR^6R^7$, —$CONR^6R^7$, —$NR^6COR^7$, —$NR^6CONR^7R^8$, —$COR^6$, —$C(O)OR^6$, —$SO_2R^6$, —$SO_2NR^6R^7$, —$NR^6SO_2R^7$, —$NR^6SO_2NR^7R^8$, —$NR^6C(O)OR^7$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^2$-$R^6$, -$Q^2$-$NR^6CONR^7R^8$, -$Q^2$-$NR^6R^7$, -$Q^2$-$COR^6$, -$Q^2$-$NR^6COR^7$, -$Q^2$-$NR^6C(O)OR^7$, -$Q^2$-$SO_2R^6$, $Q^2$-$CONR^6R^7$, -$Q^2$-$CO_2R^6$, -$Q^2$-$SO_2NR^6R^7$, -$Q^2$-$NR^6SO_2R^7$ and -$Q^2$-$NR^6SO_2NR^7R^8$; wherein $Q^2$ represents a covalent bond, an oxygen atom, a sulphur atom, —SO—, —$SO_2$—, —CO—, optionally substituted $C_1$-$C_6$ alkylene or optionally substituted $C_2$-$C_6$ alkenylene; and $R^6$, $R^7$, $R^8$ each independently represent hydrogen, optionally substituted $C_1$-$C_6$ alkyl, optionally substituted heterocyclyl, optionally substituted heteroaryl, optionally substituted aryl, or an optionally substituted cycloalkyl.

In one aspect, the invention also relates to pharmaceutical compositions comprising the compounds of the present invention and one or more pharmaceutically acceptable excipients.

In another aspect, the compounds of the invention are useful for the treatment of cancer.

BRIEF DESCRIPTION OF THE FIGURES

FIG. 1 provides an image of Cezanne 1 purified from mammalian cells. FLAG-purified protein or the indicated concentrations of BSA were separated by SDS-PAGE and stained with Imperial (Pierce Biotechnology).

FIG. 2 is a graph showing proteolytic activity of Cezanne 1 measured using a fluorescence polarisation assay. Various volumes of purified Cezanne 1 as indicated were incubated with a TAMRA labelled peptide linked to ubiquitin via an isopeptide bond.

DETAILED DESCRIPTION OF THE INVENTION

The definitions and explanations below are for the terms as used throughout this entire document including both the specification and the claims. Reference to compounds as described herein (e.g. a compound of formula (I)), includes reference to formula (I) and (II) including any sub-generic embodiments thereof, e.g. formula (IA).

Where any group of the compounds of formula (I) have been referred to as optionally substituted, this group may be substituted or unsubstituted. Substitution may be by one or more of the specified substituents which may be the same or different. It will be appreciated that the number and nature of substituents will be selected to avoid any sterically undesirable combinations.

In the context of the present specification, unless otherwise stated an alkyl, alkylene, alkoxy, alkenyl, or alkynyl substituent (or linker) group or an alkyl, alkenyl moiety in a substituent group may be linear or branched. Alkyl, alkylene, alkenyl and alkenylene chains may also include intervening heteroatoms such as oxygen.

$C_x$-$C_y$ alkyl refers to a saturated aliphatic hydrocarbon group having x-y carbon atoms which may be linear or branched. For example $C_1$-$C_6$ alkyl contains from 1 to 6 carbon atoms and includes $C_1$, $C_2$, $C_3$, $C_4$, $C_5$ and $C_6$. "Branched" means that at least one carbon branch point is present in the group. For example, tert-butyl and isopropyl are both branched groups. Examples of $C_1$-$C_6$ alkyl groups include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. $C_1$-$C_6$ alkyl, $C_1$-$C_4$ alkyl and $C_1$-$C_3$ alkyl within the definitions of $R^{1a}$, $R^{1b}$, $R^{1c}$, $R^{1d}$, $R^{1e}$, $R^{1f}$, $R^3$, $R^4$, $R^5$, $R^6$, $R^7$, $R^8$, $Q^1$, and within the definition of substituents for $R^2$, may be unsubstituted or substituted with one or more of the substituents defined herein. Examples of substituted $C_1$-$C_6$ alkyl therefore include $CF_3$, $CH_2CF_3$, $CH_2CN$, $CH_2OH$ and $CH_2CH_2OH$.

A $C_x$-$C_y$ alkylene group or moiety may be linear or branched and refers to a divalent hydrocarbon group having one less hydrogen atom from $C_x$-$C_y$ alkyl as defined above. $C_1$-$C_6$ alkylene may include intervening heteroatoms such as oxygen, and therefore includes alkyleneoxy groups. Alkyleneoxy as employed herein also extends to embodiments in which the or an oxygen atom (e.g. a single oxygen atom) is located within the alkylene chain, for example $CH_2CH_2OCH_2$ or $CH_2OCH_2$. Examples of $C_1$-$C_6$ alkylene groups include methylene, methyleneoxy, ethylene, ethyleneoxy, n-propylene, n-propyleneoxy, n-butylene, n-butyleneoxy, methylmethylene and dimethylmethylene. Unless stated otherwise, $C_1$-$C_6$ alkylene, $C_1$-$C_4$ alkylene and $C_1$-$C_3$ alkylene within the definitions of $R^3$, $R^4$, $R^5$, $Q^1$ and $Q^2$ may be unsubstituted or substituted with one or more of the substituents defined herein.

$C_2$-$C_6$ alkenyl refers to a linear or branched hydrocarbon chain radical containing at least two carbon atoms and at least one double bond and includes $C_2$-$C_4$ alkenyl. Examples of alkenyl groups include ethenyl, propenyl, 2-propenyl, 1-butenyl, 2-butenyl, 1-hexenyl, 2-methyl-1-propenyl, 1,2-butadienyl, 1,3-pentadienyl, 1,4-pentadienyl and 1-hexadienyl. Unless stated otherwise, $C_2$-$C_6$ alkenyl and $C_2$-$C_4$ alkenyl within the definitions of $Q^1$ and within the definition of substituents for $R^2$, may be unsubstituted or substituted with one or more of the substituents defined herein.

$C_2$-$C_6$ alkenylene refers to linear or branched hydrocarbon group having one less hydrogen atom from $C_2$-$C_6$ alkenyl as defined above. Examples of $C_2$-$C_6$ alkenylene include ethenylene, propenylene and butenylene. Unless stated otherwise, $C_2$-$C_6$ alkenylene and $C_2$-$C_4$ alkenylene within the definition of substituents for $Q^1$ and $Q^2$, may be unsubstituted or substituted with one or more of the substituents defined herein.

$C_2$-$C_6$ alkynyl refers to a linear or branched hydrocarbon chain radical containing at least two carbon atoms and at least one triple bond. Examples of alkenyl groups include ethynyl, propynyl, 2-propynyl, 1-butynyl, 2-butynyl and 1-hexynyl. Unless specified otherwise, $C_2$-$C_6$ alkynyl, within the definitions of $Q^1$ and within the definition of substituents for $R^2$, may be unsubstituted or substituted with one or more of the substituents defined herein.

$C_1$-$C_6$ alkoxy refers to a group or part of a group having an —O—$C_x$-$C_y$ alkyl group according to the definition of $C_x$-$C_y$ alkyl above. $C_1$-$C_6$ alkoxy contains from 1 to 6 carbon atoms and includes $C_1$, $C_2$, $C_3$, $C_4$, $C_5$ and $C_6$. Examples of $C_1$-$C_6$ alkoxy include methoxy, ethoxy, propoxy, isopropoxy, butoxy, pentoxy and hexoxy. Alkoxy as employed herein also extends to embodiments in which the or an oxygen atom (e.g. a single oxygen atom) is located within the alkyl chain, for example $CH_2CH_2OCH_3$ or $CH_2OCH_3$. Thus the alkoxy may be linked through carbon to the remainder of the molecule, for example, $—CH_2CH_2OCH_3$, or alternatively, the alkoxy is linked through oxygen to the remainder of the molecule, for example $—OC_{1-6}$ alkyl. In certain instances, the alkoxy may be linked through oxygen to the remainder of the molecule but the alkoxy group contains a further oxygen atom, for example $—OCH_2CH_2OCH_3$. Unless specified otherwise, $C_1$-$C_6$ alkoxy and $C_1$-$C_3$ alkoxy within the definitions $R^{1e}$, $R^{1f}$, $Q^1$, and within the definition of substituents for $R^2$, may be unsubstituted or substituted with one or more of the substituents defined herein. Examples of substituted $C_1$-$C_6$ alkoxy therefore include $OCF_3$, $OCHF_2$, $OCH_2CF_3$, $CH_2CH_2OCH_3$ and $CH_2CH_2OCH_2CH_3$.

The term "halogen" or "halo" refers to chlorine, bromine, fluorine or iodine atoms, in particular chlorine or fluorine atoms.

The term "oxo" means =O.

For the avoidance of doubt it will be understood that the cycloalkyl, heterocyclyl, aryl and heteroaryl rings disclosed herein and within the definitions of $R^{1a}$, $R^{1b}$, $R^{1c}$, $R^{1d}$, $R^{1e}$, $R^{1f}$, $R^2$, $R^6$, $R^7$, $R^8$, ring A, and within the definition of substituents for $R^2$, do not include any unstable ring structures or, in the case of heteroaryl and heterocyclic rings systems, any O—O, O—S or S—S bonds. The ring systems may be monocyclic or bicyclic. Bicyclic ring systems include bridged, fused and spiro ring systems. A substituent if present may be attached to any suitable ring atom which may be a carbon atom or, in the case of heteroaryl and heterocyclic ring systems, a heteroatom. Substitution on a ring may also include a change in the ring atom at the position of the substitution. For example, substitution on a phenyl ring may include a change in the ring atom at the position of substitution from carbon to nitrogen, resulting in a pyridine ring.

"cycloalkyl" refers to a monocyclic saturated or partially unsaturated, non-aromatic ring, wherein all of the ring atoms are carbon, and having the number of ring atoms as indicated. For example $C_3$-$C_{10}$ cycloalkyl refers to a monocyclic or bicyclic hydrocarbon ring containing 3 to 10 carbon atoms. Examples of $C_3$-$C_{10}$ cycloalkyl are cyclopropyl, cyclobutyl, cyclopentyl, cyclohexyl, cycloheptyl, cyclooctyl and decahydronaphthalenyl. Bicyclic cycloalkyl groups include bridged ring systems such as bicycloheptane and bicyclooctane. Unless specified otherwise, cycloalkyl within the definitions of $R^{1a}$, $R^{1b}$, $R^{1c}$, $R^{1d}$, $R^{1e}$, $R^{1f}$, $R^2$, $R^6$, $R^7$, $R^8$, and within the definition of substituents for $R^2$, may be unsubstituted or substituted with one or more of the substituents defined herein.

An "aryl" group/moiety refers to any monocyclic or bicyclic hydrocarbon group comprising at least one aromatic group and having from 5 to 10 carbon atom ring members. Examples of aryl groups include phenyl and naphthyl. Bicyclic rings may be fused aromatic rings where both rings are aromatic, for example, naphthalenyl. Preferred aryl groups are phenyl and naphthyl, more preferably 5 phenyl. Unless specified otherwise, aryl within the definitions of $R^{1e}$, $R^{1f}$, $R^2$, $R^6$, $R^7$, $R^8$, ring A, and within the definition of substituents for $R^2$, may be unsubstituted or substituted with one or more of the substituents defined herein.

"Heteroaryl" as used herein means a polyunsaturated, monocyclic or bicyclic 5 to 10 membered aromatic moiety containing at least one and up to 5 heteroatoms, particularly 1, 2 or 3 heteroatoms selected from N, O and S, and the remaining ring atoms are carbon atoms, in stable combinations known to the skilled person. Heteroaryl ring nitrogen and sulphur atoms are optionally oxidised, and the nitrogen atom(s) are optionally quaternized. A heteroaryl ring can be a single aromatic ring or a fused bicyclic ring where the bicyclic ring system can be aromatic, or one of the fused rings is aromatic and the other is at least partially saturated. In one example, a bicyclic heteroaryl is one in which the entire fused ring system is aromatic. Examples of fused rings where one of the rings is aromatic and the other is at least partially saturated include tetrahydropyridopyrazinyl, tetrahydroquinolinyl and tetrahydroisoquinolinyl. In such instances, attachment of the bicyclic ring to the group it is a substituent of relative to the cyanopyrrolidine core, e.g. attachment of ring A via the amide group, is from the aromatic ring of the bicycle. A bicyclic heteroaryl can have the at least one heteroatom in either of the fused rings. For example, a bicyclic ring with an aromatic ring fused to a partially saturated ring may contain the at least one heteroatom in the aromatic ring or the partially saturated ring. Attachment of the bicyclic ring to the group it is a substituent of may be via either a heteroatom containing ring or a carbon only containing ring. The point of attachment of heteroaryl to the group it is a substituent of can be via a carbon atom or a heteroatom (e.g. nitrogen). Examples of heteroaryl rings include pyridinyl, pyrazinyl, pyrimidinyl, pyridazinyl, furyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydrophyridinyl, dihydropyrrolopyridinyl, indolinyl, isoindolinyl, quinoxalinyl, benzomorpholinyl, tetrahydropyridopyrazinyl, tetrahydroquinolinyl and tetrahydroisoquinolinyl. Unless specified otherwise, heteroaryl within the definitions of $R^{1e}$, $R^{1f}$, $R^2$, $R^6$, $R^7$, $R^8$, ring A, and within the definition of substituents for $R^2$, may be unsubstituted or substituted with one or more of the substituents defined herein.

"Heterocyclyl" or "heterocyclic" as used herein in describing a ring means, unless otherwise stated, a monocyclic saturated or partially unsaturated, non-aromatic ring or a bicyclic saturated or partially unsaturated ring, wherein the bicyclic ring system is non-aromatic, the mono- or bicyclic ring having, for example, 3 to 10 members, where at least one member and up to 5 members, particularly 1, 2 or 3 members of the ring are heteroatoms selected from N, O and S, and the remaining ring atoms are carbon atoms, in stable combinations known to those of skill in the art. For example, $R^2$ and $R^3$ may together form a heterocyclic ring which incorporates the amine nitrogen. Heterocyclic ring nitrogen and sulphur atoms are optionally oxidised, and the nitrogen atoms(s) are optionally quaternized. As used herein, the heterocyclic ring may be a fused ring to another ring system to form a bicycle, i.e. one or two of the heterocyclic ring carbons is common to an additional ring system. In instances where the heterocylcyl is a bicyclic ring, the second ring can be aromatic, e.g. a fused phenyl, pyridyl, pyrazolyl, or the like. The bicyclic heterocyclyl can have at least one heteroatom in either of the fused rings. The heterocyclyl may be linked through carbon or a heteroatom to the remainder of the molecule and in instances where the heterocylyl is a bicyclic ring, the link may be via the heteroatom containing ring or the fused ring. In instances where the heterocyclyl is a bicyclic ring where the second ring is aromatic, attachment of the bicyclic group to the group it is a substituent of relative to the cyanopyrrolidine core is from the non-aromatic ring. Examples of heterocyclyl groups include azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, benzomorpholinyl and tetrahydroisoquinolinyl. Unless specified otherwise, heterocyclyl within the definitions of $R^2$, $R^6$, $R^7$, $R^8$ and within the definition of substituents for $R^2$, may be unsubstituted or substituted with one or more of the substituents defined herein. Examples of substituted heterocyclyl rings include for example 4,5-dihydro-1H-maleimido, tetramethylenesulfoxide and hydantoinyl.

"Optionally substituted" as applied to any group means that the said group may if desired be substituted with one or more substituents (e.g., 1, 2, 3 or 4 substituents) which may be the same or different.

Examples of suitable substituents for "substituted" and "optionally substituted" $C_1$-$C_6$ alkyl (including $C_1$-$C_4$ alkyl, $C_1$-$C_3$ alkyl and $C_1$-$C_2$ alkyl) and $C_1$-$C_6$ alkoxy (including $C_1$-$C_4$ alkoxy, $C_1$-$C_3$ alkoxy and $C_1$-$C_2$ alkoxy) and $C_2$-$C_6$ alkenyl (including $C_2$-$C_4$ alkenyl) and $C_2$-$C_6$ alkynyl (including $C_2$-$C_4$ alkynyl), for example within the definitions of $R^{1a}$, $R^{1b}$, $R^{1c}$, $R^{1d}$, $R^{1e}$, $R^{1f}$, $R^3$, $R^4$, $R^5$, $R^6$, $R^7$, $R^8$, $Q^1$, and within the definition of substituents for $R^2$, and $C_1$-$C_6$ alkylene (including $C_1$-$C_3$ alkylene) and $C_2$-$C_6$ alkenylene, for example within the definitions of $R^3$, $R^4$, $R^5$, $Q^1$ and $Q^2$, include halogen, hydroxyl, thiol, cyano, amino, nitro and $SF_5$ (a known mimetic of nitro), in particular, halogen (preferably fluorine or chlorine), hydroxyl and cyano.

Examples of suitable substituents for "substituted" and "optionally substituted" rings, i.e. cycloalkyl, heterocyclyl, aryl and heteroaryl rings, for example within the definitions of $R^{1a}$, $R^{1b}$, $R^{1c}$, $R^{1d}$, $R^{1e}$, $R^{1f}$, $R^2$, $R^6$, $R^7$, $R^8$, ring A, and within the definition of substituents for $R^2$, include halogen, cyano, oxo, nitro, amino, hydroxy, $C_1$-$C_6$ alkyl or $C_1$-$C_3$ alkyl, $C_1$-$C_6$ alkoxy or $C_1$-$C_3$ alkoxy, aryl, heteroaryl, heterocyclyl, $C_3$-$C_6$ cycloalkyl, $C_{1-3}$ alkylamino, $C_{2-6}$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carboxamidyl, carbamoyl, mono-$C_{1-3}$ carbamoyl, di-$C_{1-3}$ carbamoyl or any of the above in which a hydrocarbyl moiety is itself substituted by halogen, e.g. fluorine, hydroxyl, cyano, amino, nitro or $SF_5$ (a known mimetic of nitro). In groups containing an oxygen atom such as hydroxy and alkoxy, the oxygen atom can be replaced with sulphur to make groups such as thio (SH) and thio-alkyl (S-alkyl). Optional substituents therefore include groups such as S-methyl. In thio-alkyl groups, the sulphur atom may be further oxidised to make a sulfoxide or sulfone, and thus optional substituents therefore includes groups such as S(O)-alkyl and $S(O)_2$-alkyl.

Examples of suitable substituents for "substituted" and "optionally substituted" rings include in particular, fluorine, chlorine, oxo, cyano, $C_1$-$C_3$ alkyl, $C_1$-$C_3$ alkoxy, heterocyclyl, cycloalkyl, heteroary or aryl, wherein the alkyl or alkoxy is optionally substituted with one or more (e.g. one, two or three) substituents selected from halogen, hydroxyl, thiol, cyano, amino, nitro and $SF_5$.

Substituted groups thus include for example Br, Cl, F, CN, Me, Et, Pr, Bu, i-Bu, OMe, OEt, OPr, $C(CH_3)_3$, $CH(CH_3)_2$, $CF_3$, $OCF_3$, $C(O)NHCH_3$, cyclopropyl, phenyl, etc. In the case of aryl groups, the substitutions may be in the form of rings from adjacent carbon atoms in the aryl ring, for example cyclic acetals such as O—$CH_2$—O.

The term "treat" or "treating" or "treatment" includes prophylaxis and means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and non-human animals.

The dose of the compound is that amount effective to prevent occurrence of the symptoms of the disorder or to treat some symptoms of the disorder from which the patient suffers. By "effective amount" or "therapeutically effective amount" or "effective dose" is meant that amount sufficient to elicit the desired pharmacological or therapeutic effects, thus resulting in effective prevention or treatment of the disorder. Prevention of the disorder is manifested by delaying the onset of the symptoms of the disorder to a medically significant extent. Treatment of the disorder is manifested by a decrease in the symptoms associated with the disorder or an amelioration of the reoccurrence of the symptoms of the disorder.

Pharmaceutically acceptable salts of the compounds of the invention include but are not limited to addition salts (for example phosphates, nitrates, sulphates, borates, acetates, maleates, citrates, fumarates, succinates, methanesulphonates, benzoates, salicylates and hydrohalides), salts derived from organic bases (such as lithium, potassium and sodium), salts of amino acids (such as glycine, alanine, valine, leucine, isoleucine, cysteine, methionine and proline), inorganic bases (such as triethylamine, hydroxide, choline, thiamine and N—N'-diacetylethylenediamine). Other pharmaceutically acceptable salts include ammonium salts, substituted ammonium salts and aluminium salts. Further pharmaceutically acceptable salts include quaternary ammonium salts of the compounds of the invention.

General methods for the production of salts are well known to the person skilled in the art. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Where compounds of the invention exist in different enantiomeric and/or diastereoisomeric forms, the invention relates to these compounds prepared as isomeric mixtures or racemates whether present in an optically pure form or as mixtures with other isomers. Enantiomers differ only in their ability to rotate plane-polarized light by equal amounts in opposite directions and are denoted as the (+)/(S) or (−)/(R) forms respectively. Individual enantiomers or isomers may be prepared by methods known in the art, such as optical resolution of products or intermediates (for example chiral chromatographic separation e.g. chiral HPLC, or an asymmetric synthesis approach). Similarly where compounds of the invention exist as alternative tautomeric forms e.g. keto/enol, amide/imidic acid, the invention relates to the individual tautomers in isolation, and to mixtures of the tautomers in all proportions.

Included herein is the compound according to formula (II)

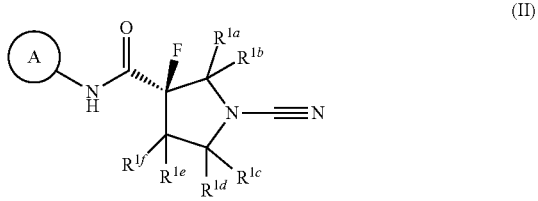

(II)

or a pharmaceutically acceptable salt thereof, wherein:

$R^{1a}$, $R^{1b}$, $R^{1c}$ and $R^{1d}$ each independently represent hydrogen or an optionally substituted $C_1$-$C_6$ alkyl, or $R^{1a}$ is linked to $R^{1b}$ to form an optionally substituted cycloalkyl ring, or $R^{1d}$ is linked to $R^{1c}$ or $R^{1e}$ to form an optionally substituted cycloalkyl ring;

$R^{1e}$ and $R^{1f}$ each independently represent hydrogen, fluorine, cyano, hydroxyl, amino, optionally substituted $C_1$-$C_6$ alkyl, optionally substituted $C_1$-$C_6$ alkoxy or an optionally substituted 5 or 6 membered ring, or $R^{1e}$ and $R^{1f}$ together form an optionally substituted cycloalkyl ring, or $R^{1e}$ is linked to $R^{1d}$ to form an optionally substituted cycloalkyl ring;

A is an optionally substituted 5 to 10 membered heteroaryl or aryl ring.

Isotopes

The compounds described herein may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. Examples of isotopes include $^2H$, $^3H$, $^{11}C$, $^{13}C$, $^{14}C$, $^{36}C$, $^{18}F$, $^{123}I$, $^{125}I$, $^{13}N$, $^{15}N$, $^{15}O$, $^{17}O$, $^{18}O$, $^{32}P$ and $^{35}S$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment, the compounds contain no radioactive isotopes. Such compounds are preferred for therapeutic use. In another embodiment, however, the compounds may contain one or more radioisotopes. Compounds containing such radioisotopes may be useful in a diagnostic context.

Certain isotopically labelled compounds of formula (I), for example, those incorporating a radioactive isotope, are useful in drug and/or substrate tissue distribution studies. The radioactive isotopes i.e. $^3H$ and $^{14}C$ are particularly useful for this purpose in view of their ease of incorporation and ready means of detection. Substitution with heavier isotopes i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining receptor occupancy. Isotopically labelled compounds of formula (I) can generally be prepared by conventional techniques known to those skilled in the art or by processes analogous to those described in the accompanying examples and preparations using an appropriate isotopically labelled reagent in place of the non-labelled reagent previously employed.

Crystalline and Amorphous Forms

The compounds of formula (I) may exist in crystalline or amorphous form and some of the crystalline forms may exist as polymorphs, which are included within the scope of the present invention. Polymorphic forms of compounds of formula (I) may be characterised and differentiated using a number of conventional analytical techniques, including, but not limited to, infra-red spectra, Raman spectra, X-ray powder diffraction, differential scanning calorimetry, thermogravimetric analysis and solid state nuclear magnetic resonance.

Accordingly, in further embodiments, the invention provides a compound according to any described embodiments in a crystalline form. The compound may be from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline. The compound may alternatively be in an amorphous form.

The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

The invention relates to any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

The invention relates to pharmaceutically functional derivatives of compounds as defined herein including ester derivatives and/or derivatives that have, or provide for, the same biological function and/or activity as any relevant compound of the invention. Thus, for the purposes of this invention, the term also includes prodrugs of compounds as defined herein.

The term "prodrug" of a relevant compound includes any compound that, following oral or parenteral administration, is metabolised in vivo to form that compound in an experimentally-detectable amount, and within a predetermined time (e.g. within a dosing interval of between 6 and 24 hours (i.e. once to four times daily).

Prodrugs of compounds may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds wherein a hydroxyl, amino, sulfhydryl, carboxyl or carbonyl group in a compound is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, ester groups of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

Compounds of the invention may be metabolised in vivo. Metabolites of compounds of formula (I) are also within the scope of the present invention. The term 'metabolites' refers to all molecules derived from any of the compounds according to the present invention in a cell or organism, preferably mammal. Preferably the term relates to molecules which differ from any molecule which is present in any such cell or organism under physiological conditions.

A treatment defined herein may be applied as a sole therapy of may involve, in addition to the compounds of the invention, conventional surgery or radiotherapy or chemotherapy. Furthermore, compounds of formula (I) can also be used in combination with existing therapeutic agents for the treatment of conditions associated with cancer, including small molecule therapeutics or antibody based therapeutics.

The compounds described herein are characterised by a cyanopyrrolidine core with an amide group and fluorine attached to the same position on the cyannopyrrolidine ring, wherein the amide group is substituted with an optionally substituted aryl or heteroaryl ring.

In accordance with a first aspect of the invention there is provided a compound of formula (I)

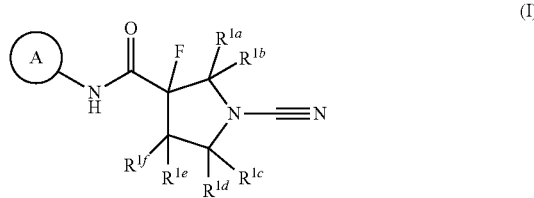

(I)

or a pharmaceutically acceptable salt thereof, wherein:
$R^{1a}$, $R^{1b}$, $R^{1c}$ and $R^{1d}$ each independently represent hydrogen or an optionally substituted $C_1$-$C_6$ alkyl, or $R^{1a}$ is linked to $R^{1b}$ to form an optionally substituted $C_3$-$C_6$ cycloalkyl ring, or $R^{1d}$ is linked to $R^{1c}$ or $R^{1e}$ to form an optionally substituted $C_3$-$C_6$ cycloalkyl ring;

$R^{1e}$ and $R^{1f}$ each independently represent hydrogen, fluorine, cyano, hydroxyl, amino, optionally substituted $C_1$-$C_6$ alkyl, optionally substituted $C_1$-$C_6$ alkoxy or an optionally substituted 5 or 6 membered heteroaryl or aryl ring, or $R^{1e}$ and $R^{1f}$ together form an optionally substituted $C_3$-$C_6$ cycloalkyl ring, or $R^{1e}$ is linked to $R^{1d}$ to form an optionally substituted $C_3$-$C_6$ cycloalkyl ring;

A is an optionally substituted monocyclic or bicyclic 5 to 10 membered heteroaryl or aryl ring.

$R^{1a}$, $R^{1b}$, $R^{1c}$, Rid may each independently represent hydrogen or optionally substituted $C_1$-$C_6$ alkyl. In particular, $R^{1a}$, $R^{1b}$, $R^{1c}$, $R^{1d}$ may each independently represent hydrogen or $C_1$-$C_3$ alkyl (e.g. methyl or ethyl). $R^{1a}$ may be hydrogen or $C_1$-$C_3$ alkyl and $R^{1b}$ may be hydrogen. $R^{1c}$ may be hydrogen or $C_1$-$C_3$ alkyl and $R^{1d}$ may be hydrogen. The alkyl may be unsubstituted or substituted with one or more substituents selected from halogen, hydroxyl, thiol, cyano, amino, nitro and $SF_5$. In particular $R^{1a}R^{1b}$, $R^{1c}$, Rid each represent hydrogen.

$R^{1a}$ may represent hydrogen. $R^{1a}$ may represent $C_1$-$C_6$ alkyl. $R^{1a}$ may represent $C_1$-$C_3$ alkyl, for example, methyl or ethyl. When $R^{1a}$ represents $C_1$-$C_6$ alkyl, $R^{1b}$, $R^{1c}$, $R^{1d}$, $R^{1e}$ and $R^{1f}$ may each represent hydrogen. The alkyl may be unsubstituted or substituted with one or more substituents selected from halogen, hydroxyl, thiol, cyano, amino, nitro and $SF_5$, in particular fluorine.

$R^{1b}$ may represent hydrogen. $R^{1b}$ may represent $C_1$-$C_6$ alkyl. $R^{1b}$ may represent $C_1$-$C_3$ alkyl, for example, methyl or ethyl. When $R^{1b}$ represents $C_1$-$C_6$ alkyl, $R^{1a}$, $R^{1c}$, $R^{1d}$, $R^{1e}$ and $R^{1f}$ may each represent hydrogen. The alkyl may be unsubstituted or substituted with one or more substituents selected from halogen, hydroxyl, thiol, cyano, amino, nitro and $SF_5$, in particular fluorine.

$R^{1c}$ may represent hydrogen. $R^{1c}$ may represent $C_1$-$C_6$ alkyl. $R^{1c}$ may represent $C_1$-$C_3$ alkyl, for example, methyl or ethyl. When $R^{1c}$ represents $C_1$-$C_6$ alkyl, $R^{1a}$, $R^{1b}$, $R^{1d}$, $R^{1e}$ and $R^{1f}$ may each represent hydrogen. The alkyl may be unsubstituted or substituted with one or more substituents selected from halogen, hydroxyl, thiol, cyano, amino, nitro and $SF_5$, in particular fluorine.

$R^{1d}$ may represent hydrogen. $R^{1d}$ may represent $C_1$-$C_6$ alkyl. $R^{1d}$ may represent $C_1$-$C_3$ alkyl, for example, methyl or ethyl. When $R^{1d}$ represents $C_1$-$C_6$ alkyl, $R^{1a}$, $R^{1b}$, $R^{1c}$, $R^{1e}$ and $R^{1f}$ may each represent hydrogen. The alkyl may be unsubstituted or substituted with one or more substituents selected from halogen, hydroxyl, thiol, cyano, amino, nitro and $SF_5$, in particular fluorine.

Alternatively, $R^{1a}$ and $R^{1b}$ may together form a cycloalkyl ring. In addition, or alternatively, $R^{1c}$ and $R^{1d}$ may together form a cycloalkyl ring. The cycloalkyl ring can contain 3, 4, 5 or 6 atoms, in particular 3 or 4 atoms. When $R^{1b}$ and $R^{1c}$ together form a $C_3$-$C_6$ cycloalkyl ring, $R^{1a}$, $R^{1d}$, $R^{1e}$ and $R^{1f}$ may be hydrogen. When $R^{1d}$ and $R^{1e}$ together form a cycloalkyl ring, $R^{1a}$, $R^{1b}$, $R^{1c}$ and $R^{1f}$ may each be hydrogen.

$R^{1e}$ may represent hydrogen, fluorine, cyano, hydroxyl, amino, optionally substituted $C_1$-$C_6$ alkyl, optionally substituted $C_1$-$C_6$ alkoxy or an optionally substituted 5 or 6 membered heteroaryl or aryl ring. The alkyl and alkoxy may be substituted with one or more substituents selected from halogen, hydroxyl, thiol, cyano, amino, nitro and $SF_5$. The heteroaryl or aryl ring may be unsubstituted or substituted with halogen, cyano, oxo, nitro, amino, hydroxy, $C_1$-$C_6$ alkyl or $C_1$-$C_6$ alkoxy. In particular, $R^{1e}$ can represent hydrogen, fluorine, $C_1$-$C_3$ alkyl or substituted $C_1$-$C_3$ alkoxy. $R^{1e}$ can represent fluorine. $R^{1e}$ can represent methyl. $R^{1e}$ can represent methoxy. $R^{1e}$ can represent $CF_3$. $R^{1e}$ can represent $OCF_3$. When $R^{1e}$ represents fluorine, cyano, hydroxyl, amino, optionally substituted $C_1$-$C_6$ alkyl, optionally substituted $C_1$-$C_6$ alkoxy or an optionally substituted 5 or 6 membered heteroaryl or aryl ring, $R^{1a}$, $R^{1b}$, $R^{1c}$, $R^{1d}$ and $R^{1f}$ may each represent hydrogen. Alternatively, $R^{1e}$ represents hydrogen.

$R^{1f}$ may represent hydrogen fluorine, cyano, hydroxyl, amino, optionally substituted $C_1$-$C_6$ alkyl, optionally substituted $C_1$-$C_6$ alkoxy, or an optionally substituted 5 or 6 membered heteroaryl or aryl ring. The alkyl and alkoxy may be substituted with one or more substituents selected from halogen, hydroxyl, thiol, cyano, amino, nitro and $SF_5$. The heteroaryl or aryl ring may be unsubstituted or substituted with halogen, cyano, oxo, nitro, amino, hydroxy, $C_1$-$C_6$ alkyl or $C_1$-$C_6$ alkoxy. In particular, $R^{1f}$ can represent hydrogen fluorine, unsubstituted or substituted $C_1$-$C_3$ alkyl or unsubstituted or substituted $C_1$-$C_3$ alkoxy. $R^{1f}$ can represent fluorine. $R^{1f}$ can represent methyl. $R^{1f}$ can represent methoxy. $R^{1f}$ can represent $CF_3$. $R^{1f}$ can represent $OCF_3$. When $R^{1f}$ represents fluorine, cyano, hydroxyl, amino, optionally substituted $C_1$-$C_6$ alkyl or optionally substituted $C_1$-$C_6$ alkoxy or an optionally substituted 5 or 6 membered heteroaryl or aryl ring, $R^{1a}$, $R^{1b}$, $R^{1c}$, $R^{1d}$ and $R^{1e}$ may each represent hydrogen. Alternatively, $R^{1f}$ represents hydrogen.

Alternatively, $R^{1e}$ and $R^{1f}$ may together form a cycloalkyl ring. Alternatively, $R^{1e}$ and $R^{1d}$ may together form a cycloalkyl ring. The cycloalkyl ring can contain 3, 4, 5 or 6 atoms, in particular 3 or 4 atoms. When $R^{1e}$ and $R^{1f}$ together form a $C_3$-$C_6$ cycloalkyl ring, $R^{1a}$, $R^{1b}$, $R^{1c}$ and $R^{1d}$ may be hydrogen. When $R^{1e}$ and $R^{1d}$ together form a cycloalkyl ring, $R^{1a}$, $R^{1b}$, $R^{1c}$ and $R^{1f}$ may each be hydrogen.

The cycloalkyl rings within the definitions of $R^{1a}$, $R^{1b}$, $R^{1c}$, $R^{1d}$, $R^{1e}$ and $R^{1f}$ may be unsubstituted or substituted with one or more substituents selected from halogen, cyano, oxo, nitro, amino, hydroxy, $C_1$-$C_3$ alkyl, $C_1$-$C_3$ alkoxy, $C_{1-3}$ alkylamino, $C_{2-6}$ alkenylamino, $C_1$-$C_3$ acylamino, carboxy, $C_1$-$C_3$ alkoxycarbonyl, carboxamidyl, carbamoyl, wherein any hydrocarbyl moiety may itself be substituted by one or more halogen, in particular fluorine. In particular, the cycloalkyl ring may be unsubstituted or substituted with one or two substituents selected from halogen, cyano, oxo, nitro, amino, hydroxy, $C_1$-$C_3$ alkyl and $C_1$-$C_3$ alkoxy, wherein the alkyl and alkoxy may be substituted with one or more halogen, in particular fluorine.

One of $R^{1a}$, $R^{1b}$, $R^{1c}$, $R^{1d}$, $R^{1e}$ and $R^{1f}$ may be other than hydrogen, and the remaining are each hydrogen.

Two of $R^{1a}$, $R^{1b}$, $R^{1c}$, $R^{1d}$, $R^{1e}$ and $R^{1f}$ may be other than hydrogen, and the remaining are each hydrogen.

Three of $R^{1a}$, $R^{1b}$, $R^{1c}$, $R^{1d}$, $R^{1e}$ and $R^{1f}$ may be other than hydrogen, and the remaining are each hydrogen.

Four of $R^{1a}$, $R^{1b}$, $R^{1c}$, $R^{1d}$, $R^{1e}$ and $R^{1f}$ may be other than hydrogen, and the remaining are each hydrogen.

Five of $R^{1a}$, $R^{1b}$, $R^{1c}$, $R^{1d}$, $R^{1e}$ and $R^{1f}$ may be other than hydrogen, and the remaining are each hydrogen.

Six of $R^{1a}$, $R^{1b}$, $R^{1c}$, $R^{1d}$, $R^{1e}$ and $R^{1f}$ may be other than hydrogen, and the remaining are each hydrogen.

When one, two, three, four, five or six of $R^{1a}$, $R^{1b}$, $R^{1c}$, $R^{1d}$, $R^{1e}$ and $R^{1f}$ are other than hydrogen, the remaining R groups represent a group in accordance with the definitions above. In particular, one, two, three or four of $R^{1a}$, $R^{1b}$, $R^{1c}$, $R^{1d}$, $R^{1e}$ and $R^{1f}$ may be other than hydrogen and the remaining each represent hydrogen. More particularly, one or two of $R^{1a}$, $R^{1b}$, $R^{1c}$, $R^{1d}$, $R^{1e}$ and $R^{1f}$ may be other than hydrogen and the remaining each represent hydrogen.

The compounds may be in the form where $R^{1a}$, $R^{1b}$, $R^{1c}$, $R^{1d}$, $R^{1e}$ and $R^{1f}$ are each hydrogen. In such cases the compounds may be of formula (IA):

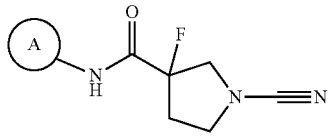

(IA)

or a pharmaceutically acceptable salt thereof, wherein A is an optionally substituted 5 to 10 membered heteroaryl or aryl ring.

The heteroaryl or aryl ring of ring A may be defined according to the definition of heteroaryl and aryl ring found herein and may be monocyclic or bicyclic. Where the ring is bicyclic, the second ring may be aromatic, or may be partly saturated, and thus not every atom in the 5 to 10 membered ring need be in an aryl system, there must be at least one aryl or heteroaryl ring within the 5 to 10 atoms, and it is this ring that is attached to the amide nitrogen.

A represents a 5 to 10 membered (e.g. 5, 6, 7, 8, 9 or 10 membered) monocyclic or fused bicyclic heteroaryl or aryl ring which may be optionally substituted with one or more (e.g. one, two, three or four) of -$Q^1$-$(R^2)_n$, in particular one or two of -$Q^1$-$(R^2)_n$.

In particular, A may represent a 5 or 6 membered heteroaryl or aryl ring which may be optionally substituted with one or more (e.g. one, two, three or four) of -$Q^1(R^2)_n$.

Alternatively, A may represent a 9 or 10 membered bicyclic heteroaryl or aryl ring which may be optionally substituted with one or more (e.g. one, two, three or four) of -$Q^1(R^2)_n$.

When A is a heteroaryl ring, the ring may be monocyclic or bicyclic and comprise one or more (e.g. 1, 2 or 3) heteroatoms independently selected from nitrogen, oxygen and sulphur. In particular, the heteroaryl ring may contain at least one nitrogen atom, for example, 1, 2 or 3 nitrogen atoms, preferably 1 or 2 nitrogen heteroatoms. Examples of nitrogen containing heteroaryl rings include pyridinyl, pyrazinyl, pyrimidinyl, pyridazinyl, pyrrolyl, oxazolyl, thiazolyl, pyrazolyl, triazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzimidazolyl, benzothiazolyl, napthyridinyl, pteridinyl, pyrazinyl, 4H-quinolizinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydropyridinyl, quinoxalinyl, benzomorpholinyl, dihydropyrrolopyridinyl, tetrahydropyridopyrazinyl, tetrahydroquinolinyl and tetrahydroisoquinolinyl.

For example, nitrogen containing heteroaryl rings include pyridinyl, pyrazinyl, pyrimidinyl, pyridazinyl, pyrrolyl, oxazolyl, thiazolyl, pyrazolyl, triazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzimidazolyl, benzothiazolyl, napthyridinyl, pteridinyl, pyrazinyl, 4H-quinolizinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydropyridinyl, quinoxalinyl and benzomorpholinyl.

The optionally substituted 5 to 10 membered heteroaryl or aryl ring may be selected from pyridinyl, pyrazinyl, pyrimidinyl, pyridazinyl, furyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydropyridinyl, dihydropyrrolopyridinyl, indolinyl, isoindolinyl, quinoxalinyl, benzomorpholinyl, tetrahydropyridopyrazinyl, tetrahydroquinolinyl, tetrahydroisoquinolinyl, phenyl, naphthyl and naphthalenyl.

For example, the optionally substituted 5 to 10 membered heteroaryl or aryl ring may be selected from pyridinyl, pyrazinyl, pyrimidinyl, pyridazinyl, furyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydrophyridinyl, quinoxalinyl, benzomorpholinyl, phenyl, naphthyl and naphthalenyl.

In instances where ring A is a fused bicyclic ring where one of the rings is aromatic and the other is at least partially saturated, attachment to the cyanopyrrolidine ring via the amide is from the aromatic ring of the bicycle.

In particular, ring A is selected from thiazolyl, imidazolyl, isoxazolyl, pyrazolyl, phenyl, benzothiazolyl, imidazopyridinyl and quinolinyl.

In all cases described herein, ring A may be unsubstituted or substituted with one or more -$Q^1$-($R^2$)$_n$ wherein each occurrence of -$Q^1$-($R^2$)$_n$ is the same or different, and wherein:

n is 0 or 1;

$Q^1$ represents halogen, cyano, oxo, nitro, —$OR^3$, —$SR^3$, —$NR^3R^4$, —$CONR^3R^4$, —$NR^3COR^4$, —$NR^3CONR^4R^5$, —$COR^3$, —$C(O)OR^3$, —$SO_2R^3$, —$SO_2NR^3R^4$, —$NR^3SO_2R^4$, —$NR^3SO_2NR^4R^5$, —$NR^3C(O)OR^4$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, a covalent bond, an oxygen atom, a sulphur atom, —SO—, —$SO_2$—, —CO—, —C(O)O—, —$CONR^3$—, —$NR^3$—, —$NR^3CO$—, —$NR^3CONR^4$—, —$SO_2NR^3$—, —$NR^3SO_2$—, —$NR^3SO_2NR^4$—, —$NR^3C(O)O$—, —$NR^3C(O)OR^4$—, optionally substituted $C_1$-$C_6$ alkylene or optionally substituted —$C_2$-$C_6$ alkenylene;

$R^3$, $R^4$ and $R^5$ each independently represent hydrogen, optionally substituted $C_1$-$C_6$ alkyl or optionally substituted $C_1$-$C_6$ alkylene.

When n is 1, $R^2$ represents an optionally substituted 3 to 10 membered heterocyclyl, cycloalkyl, heteroaryl or aryl ring (when n is 0, $Q^1$ is present and $R^2$ is absent).

Ring A may be unsubstituted or substituted with one, two, three or four of -$Q^1$-($R^2$)$_n$.

In particular, ring A is either unsubstituted or substituted with one or two of -$Q^1$-($R^2$)$_n$. Each occurrence of -$Q^1$-($R^2$)$_n$ may be the same or different. Alternatively, ring A may be either unsubstituted or substituted with one of -$Q^1$-($R^2$)$_n$. $Q^1$, $R^2$ and n are as defined herein.

In all cases described herein, $Q^1$ may be selected from halogen (e.g. fluorine, chlorine or bromine), cyano, oxo, nitro, —$OR^3$ (e.g hydroxyl), —$SR^3$ (e.g. thiol), —$NR^3R^4$ (e.g. amino or N,N-dimethylamino), —$CONR^3R^4$ (e.g. amido), —$NR^3COR^4$ (N-acetyl), —$NR^3CONR^4R^5$, —$COR^3$ (e.g. acetyl), —$C(O)OR^3$ (e.g. methoxycarbonyl or ethoxycarbonyl), —$SO_2R^3$ (e.g. methyl sulphonyl), —$SO_2NR^3R^4$ (e.g. dimethylaminosulphonyl), —$NR^3SO_2R^4$, —$NR^3SO_2NR^4R^5$, —$NR^3C(O)OR^4$, optionally substituted —$C_1$-$C_4$ alkyl (e.g. propyl, isobutyl or tert butyl), optionally substituted $C_1$-$C_2$ alkyl (e.g. methyl or eithyl), optionally substituted —$C_1$-$C_6$ alkoxy, optionally substituted —$C_2$-$C_6$ alkenyl, optionally substituted —$C_2$-$C_6$ alkynyl, a covalent bond, an oxygen atom, a sulphur atom, —SO—, —$SO_2$—, —CO—, —C(O)O—, —$CONR^3$—, —$NR^3$— (e.g. methylamino), —$NR^3CO$—, —$NR^3CONR^4$—, —$SO_2NR^3$—, —$NR^3SO_2$—, —$NR^3SO_2NR^4$—, —$NR^3C(O)O$—, —$NR^3C(O)OR^4$—, optionally substituted $C_1$-$C_4$ alkylene (e.g. methylene or ethylene) or optionally substituted —$C_2$-$C_4$ alkenylene (e.g. vinyl).

When n is 0, ring A may be substituted with one or more (e.g. one, two, three or four) $Q^1$ substituents independently selected from halogen (e.g. fluorine, chlorine or bromine), cyano, oxo, nitro, —$OR^3$, —$SR^3$, —$NR^3R^4$, —$CONR^3R^4$, —$NR^3C(O)R^4$, —$NR^3C(O)NR^4R^5$, —$C(O)R^3$, —$C(O)OR^3$, —$SO_2R^3$, —$SO_2NR^3R^4$, —$NR^3SO_2R^4$, —$NR^3SO_2NR^4R^5$, —$NR^3C(O)OR^4$, —$C_1$-$C_6$ alkyl, —$C_1$-$C_6$ alkoxy, —$C_2$-$C_6$ alkenyl, or —$C_2$-$C_6$ alkynyl, wherein alkyl, alkoxy, alkenyl or alkynyl, may be unsubstituted or substituted with one or more substituents selected from halogen, hydroxyl, thiol, cyano, amino, nitro and $SF_5$, and wherein $R^3$, $R^4$ and $R^5$ are as defined above.

In particular, when n is 0, $Q^1$ may represent halogen (e.g. fluorine or chlorine), $C_1$-$C_6$ alkyl or $C_1$-$C_3$ alkyl optionally substituted with one or more fluorine, e.g. $CF_3$.

In particular examples, n is 0 and ring A represents a 5 or 6 membered heteroaryl or aryl ring which is optionally substituted with one or more (e.g. one, two, three or four) $Q^1$ substituents independently selected from halogen (e.g. fluorine or chlorine), $C_1$-$C_6$ alkyl or $C_1$-$C_3$ alkyl optionally substituted with one or more fluorine, e.g. $CF_3$.

Alternatively, n is 0 and ring A represents a 9 or 10 membered heteroaryl or aryl ring which is optionally substituted with one or more (e.g. one, two, three or four) $Q^1$ substituents independently selected from halogen (e.g. fluorine or chlorine), $C_1$-$C_6$ alkyl or $C_1$-$C_3$ alkyl optionally substituted with one or more fluorine, e.g. $CF_3$.

When n is 1, $Q^1$ is a covalent bond or a linker selected from covalent bond, an oxygen atom, a sulphur atom, —SO—, —$SO_2$—, —CO—, —C(O)O—, —$CONR^3$—, —$NR^3$—, —$NR^3CO$—, —$NR^3CONR^4$—, —$SO_2NR^3$—, —$NR^3SO_2$—, —$NR^3SO_2NR^4$—, —$NR^3C(O)O$—, —$NR^3C(O)OR^4$—, $C_1$-$C_6$ alkylene or —$C_2$-$C_6$ alkenylene, wherein the alkylene or alkenylene is optionally substituted with one or more substituents selected from halogen, hydroxyl, thiol, cyano, amino, nitro and $SF_5$.

In particular, when n is 1, $Q^1$ is a covalent bond, an oxygen atom, $C_1$-$C_6$ alkylene or $C_1$-$C_3$ alkylene, wherein the alkylene is optionally substituted with one or more substituents selected from halogen, hydroxyl, thiol, cyano, amino, nitro and $SF_5$.

It is preferred that ring A is substituted with a further ring either directly or via a linker, i.e. ring A is substituted with at least one -$Q^1$-($R^2$)$_n$ wherein n is 1. Substitution with a further ring is especially preferred when ring A is a monocycle.

In all cases described herein, $R^2$ represents a 3 to 10 membered heterocyclyl, cycloalkyl, heteroaryl or aryl ring. $R^2$ may be selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, dihydropyrrolopyridinyl, quinoxalinyl, benzomorpholinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, tetrahydropyridopyrazinyl, thiazolidinyl, benzopyranyl, tetrahydroquinolinyl, benzomorpholinyl and tetrahydroisoquinolinyl.

For example, $R^2$ may be selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, benzomorpholinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, benzomorpholinyl and tetrahydroisoquinolinyl.

$R^2$ may represent an optionally substituted 5 or 6 membered heterocyclyl, cycloalkyl, heteroaryl or aryl ring.

Alternatively, $R^2$ may represent an optionally substituted 9 or 10 membered heterocyclyl, cycloalkyl, heteroaryl or aryl ring.

In particular, $R^2$ is selected from substituted or unsubstituted phenyl, pyrazolyl, indazolyl, imidazolyl and thiazolyl. More particularly, $R^2$ is phenyl.

In all cases described herein, $R^2$ may be optionally substituted with one or more substituents selected from halogen, cyano, oxo, nitro, —$OR^6$, —$SR^6$, —$NR^6R^7$, —$CONR^6R^7$, —$NR^6COR^7$, —$NR^6CONR^7R^8$, —$COR^6$, —$C(O)OR^6$, —$SO_2R^6$, —$SO_2NR^6R^7$, —$NR^6SO_2R^7$, —$NR^6SO_2NR^7R^8$, —$NR^6C(O)OR^7$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^2$-$R^6$, -$Q^2$-$NR^6CONR^7R^8$, -$Q^2$-$NR^6R^7$, -$Q^2$-$COR^6$, -$Q^2$-$NR^6COR^6$, -$Q^2$-$NR^6C(O)OR^7$, -$Q^2$-$SO_2R^6$, $Q^2$-$CONR^6R^7$, -$Q^2$-$CO_2R^6$, -$Q^2$-$SO_2NR^6R^7$, -$Q^2$-$NR^6SO_2R^7$ and -$Q^2$-$NR^6SO_2NR^7R^8$, wherein the alkyl, alkoxy, alkenyl or alkynyl are optionally substituted with one or more substituents selected from halogen, hydroxyl, thiol, cyano, amino, nitro and $SF_5$; wherein $Q^2$ represents a covalent bond, an oxygen atom, a sulphur atom, —SO—, —$SO_2$—, —CO—, optionally substituted $C_1$-$C_6$ alkylene or optionally substituted $C_2$-$C_6$ alkenylene; and $R^6$, $R^7$, $R^8$ each independently represent hydrogen, optionally substituted $C_1$-$C_6$ alkyl, optionally substituted heterocyclyl, optionally substituted heteroaryl, optionally substituted aryl, or an optionally substituted cycloalkyl.

$R^2$ may be substituted with one or more (e.g. one, two, three or four), in particular one or two, substituents independently selected from halogen, cyano, oxo, nitro, —$OR^6$, —$SR^6$, —$NR^6R^7$, —$CONR^6R^7$, —$NR^6COR^7$, —$NR^6CONR^7R^8$, —$COR^6$, —$C(O)OR^6$, —$SO_2R^6$, —$SO_2NR^6R^7$, —$NR^6SO_2R^7$, —$NR^6SO_2NR^7R^8$, —$NR^6C(O)OR^7$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^2$-$R^6$, -$Q^2$-$NR^6CONR^7R^8$, -$Q^2$-$NR^6R^7$, -$Q^2$-$COR^6$, -$Q^2$-$NR^6COR^7$, -$Q^2$-$NR^6C(O)OR^7$, -$Q^2$-$SO_2R^6$, -$Q^2$-$CONR^6R^7$, -$Q^2$-$CO_2R^6$, -$Q^2$-$SO_2NR^6R^7$, -$Q^2$-$NR^6SO_2R^7$ and -$Q^2$-$NR^6SO_2NR^7R^8$, wherein $Q^2$ represents a covalent bond, an oxygen atom, a sulphur atom, —SO—, —$SO_2$—, —CO—, $C_1$-$C_6$ alkylene or optionally substituted $C_2$-$C_6$ alkenylene, and wherein $R^6$, $R^7$, $R^8$ each independently represent hydrogen or optionally substituted $C_1$-$C_6$ alkyl, wherein any alkyl, alkoxy, alkenyl, alkynyl, alkylene or alkenylene is optionally substituted with one or more (e.g. one, two, three or four) substituents selected from halogen, hydroxyl, thiol, cyano, amino, nitro and $SF_5$.

In particular, $R^2$ may be substituted with one or more substituents selected from cyano, $C(O)NR^6R^7$, —$C_1$-$C_4$ alkyl (e.g. propyl, isobutyl or tert butyl) or $C_1$-$C_2$ alkyl (e.g. methyl or ethyl), and a 3 to 10 membered heterocyclyl, cycloalkyl, heteroaryl or aryl ring, wherein $R^6$ and $R^7$ each independently represent hydrogen or optionally substituted $C_1$-$C_6$ alkyl. The alkyl may be optionally substituted with one or more fluorine.

More particularly, $R^2$ may be mono-substituted with a substituent selected from cyano, $C(O)NR^6R^7$, —$C_1$-$C_3$ alkyl, in particular methyl, and imidazolyl, wherein $R^6$ and $R^7$ each independently represent hydrogen or methyl.

In addition, or alternatively, $R^2$ may be optionally substituted with a further optionally substituted 3 to 10 membered heterocyclyl, cycloalkyl, heteroaryl or aryl ring, either directly attached or via a linking group. The linking group may be an oxygen atom, a carbonyl or an optionally substituted $C_1$-$C_6$ alkylene. The linking group may be oxygen, —CO— or an alkylene chain, for example, methylene. The 3 to 10 membered ring may be unsubstituted or substituted with one or more (e.g. one, two, three of four), in particular one or two, substituents selected from halogen (for example, fluorine or chlorine), $C_1$-$C_4$ alkyl (e.g. propyl, isobutyl or tert butyl) or $C_1$-$C_2$ alkyl (e.g. methyl or ethyl) wherein the alkyl may be optionally substituted with one or more fluorine. In particular, the 3 to 10 membered ring is unsubstituted.

In particular, $R^2$ may be unsubstituted, mono-substituted or di-substituted. More particularly, $R^2$ is unsubstituted or mono-substituted.

In certain instances, $R^2$ represents a 3 to 10 membered heterocyclyl, cycloalkyl, heteroaryl or aryl ring selected from heterocyclyl, cycloalkyl, heteroaryl or aryl ring selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, benzomorpholinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, benzomorpholinyl and tetrahydroisoquinolinyl which is either unsubstituted or substituted with one or more (e.g. one, two or three) substituents selected from halogen (e.g. fluorine or chlorine), cyano, oxo, nitro, —$OR^6$, —$SR^6$, —$NR^6R^7$, —$CONR^6R^7$, —$NR^6COR^7$, —$NR^6CONR^7R^8$, —$COR^6$, —$C(O)OR^6$, —$SO_2R^6$, —$SO_2NR^6R^7$, —$NR^6SO_2R^7$, —$NR^6SO_2NR^7R^8$, —$NR^6C(O)OR^7$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^2$-$R^6$, -$Q^2$-$NR^6CONR^7R^8$, -$Q^2$-$NR^6R^7$, -$Q^2$-$COR^6$, -$Q^2$-$NR^6COR^6$, -$Q^2$-$NR^6C(O)OR^7$, -$Q^2$-$SO_2R^6$, $Q^2$-$CONR^6R^7$, -$Q^2$-$CO_2R^6$, -$Q^2$-$SO_2NR^6R^7$, -$Q^2$-$NR^6SO_2R^7$ and -$Q^2$-$NR^6SO_2NR^7R^8$, wherein the alkyl, alkoxy, alkenyl or alkynyl are optionally substituted with one or more substituents selected from halogen, hydroxyl, thiol, cyano, amino, nitro and $SF_5$, wherein $Q^2$ represents a covalent bond, an oxygen atom, a sulphur atom, —SO—, —$SO_2$—, —CO—, $C_1$-$C_6$ alkylene or optionally substituted $C_2$-$C_6$ alkenylene, and $R^6$, $R^7$, $R^8$ each independently represent hydrogen, optionally substituted $C_1$-$C_6$ alkyl, optionally substituted heterocyclyl, optionally substituted heteroaryl, optionally substituted aryl, or an optionally substituted cycloalkyl.

$R^2$ may represent a ring selected from phenyl, pyrazolyl, indazolyl, imidazolyl and thiazolyl, wherein the ring is unsubstituted or substituted with one or more, in particular one or two, substituents selected from halogen (e.g. fluorine or chlorine), cyano, oxo, nitro, —$OR^6$, —$SR^6$, —$NR^6R^7$, —$CONR^6R^7$, —$NR^6COR^7$, —$NR^6CONR^7R^8$, —$COR^6$, —$C(O)OR^6$, —$SO_2R^6$, —$SO_2NR^6R^7$, —$NR^6SO_2R^7$, —$NR^6SO_2NR^7R^8$, —$NR^6C(O)OR^7$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^2$-$R^6$, -$Q^2$-$NR^6CONR^7R^8$, -$Q^2$-$NR^6R^7$, -$Q^2$-$COR^6$, -$Q^2$-$NR^6COR^7$, -$Q^2$-$NR^6C(O)OR^7$, -$Q^2$-$SO_2R^6$, $Q^2$-$CONR^6R^7$, -$Q^2$-$CO_2R^6$, -$Q^2$-$SO_2NR^6R^7$, -$Q^2$-$NR^6SO_2R^7$ and -$Q^2$-$NR^6SO_2NR^7R^8$, wherein the alkyl, alkoxy, alkenyl or alkynyl are optionally substituted with one or more substituents selected from halogen, hydroxyl, thiol, cyano, amino, nitro and $SF_5$, wherein $Q^2$ represents a covalent bond, an oxygen atom, a sulphur atom, —SO—, —$SO_2$—, —CO—, $C_1$-$C_6$ alkylene or optionally substituted $C_2$-$C_6$ alkenylene, and $R^6$, $R^7$, $R^8$ each independently represent hydrogen, optionally substituted $C_1$-$C_6$ alkyl, optionally substituted heterocyclyl, optionally substituted heteroaryl, optionally substituted aryl, or an optionally substituted cycloalkyl.

$R^2$ may represent a ring selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, benzomorpholinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, benzomorpholinyl and tetrahydroisoquinolinyl, wherein the ring is unsubstituted or substituted with cyano, $C(O)NR^6R^7$, —$C_1$-$C_4$ alkyl (e.g. propyl, isobutyl or tert butyl) or $C_1$-$C_2$ alkyl (e.g. methyl or ethyl), and a 3 to 10 membered heterocyclyl, cycloalkyl, heteroaryl or aryl ring, wherein $R^6$ and $R^7$ each independently represent hydrogen or optionally substituted $C_1$-$C_6$ alkyl. The alkyl may be optionally substituted with one or more fluorine.

In particular, $R^2$ may be selected from phenyl, pyrazolyl, indazolyl, imidazolyl and thiazolyl wherein the ring is unsubstituted or substituted with one or more (e.g. one, two or three) substitutents selected from cyano, $C(O)NR^6R^7$, —$C_1$-$C_6$ alkyl, and a 3 to 10 membered heterocyclyl, cycloalkyl, heteroaryl or aryl ring, wherein $R^6$ and $R^7$ each independently represent hydrogen or optionally substituted $C_1$-$C_6$ alkyl.

The present invention further relates to compounds of formula (I), or a pharmaceutically acceptable salt thereof, wherein:

$R^{1a}$, $R^{1b}$, $R^{1c}$ and $R^{1d}$ each independently represent hydrogen or $C_1$-$C_3$ alkyl which may be optionally substituted with one or more fluorine;

$R^{1e}$ and $R^{1f}$ independently represent hydrogen, fluorine, $C_1$-$C_3$ alkyl or $C_1$-$C_3$ alkoxy, wherein the alkyl or alkoxy may be optionally substituted with one or more fluorine;

A represents a 5 to 10 membered monocyclic or bicyclic heteroaryl or aryl ring which is unsubstituted or substituted with one, two or three of -$Q^1$-$(R^2)_n$;

n is 0 or 1;

$Q^1$, $R^2$ and n are as defined herein.

In particular, $Q^1$ is selected from halogen (e.g. fluorine, chlorine or bromine), cyano, oxo, nitro, —$OR^3$ (e.g hydroxyl), —$SR^3$ (e.g. thiol), —$NR^3R^4$ (e.g. amino or N,N-dimethylamino), —$CONR^3R^4$ (e.g. amido), —$NR^3COR^4$ (N-acetyl), —$NR^3CONR^4R^5$, —$COR^3$ (e.g. acetyl), —$C(O)OR^3$ (e.g. methoxycarbonyl or ethoxycarbonyl), —$SO_2R^3$ (e.g. methyl sulphonyl), —$SO_2NR^3R^4$ (e.g. dimethylaminosulphonyl), —$NR^3SO_2R^4$, —$NR^3SO_2NR^4R^5$, —$NR^3C(O)OR^4$, optionally substituted —$C_1$-$C_4$ alkyl (e.g. propyl, isobutyl or tert butyl), optionally substituted $C_1$-$C_2$ alkyl (e.g. methyl or eithyl), optionally substituted —$C_1$-$C_6$ alkoxy, optionally substituted —$C_2$-$C_6$ alkenyl, optionally substituted —$C_2$-$C_6$ alkynyl, a covalent bond, an oxygen atom, a sulphur atom, —SO—, —$SO_2$—, —CO—, —C(O)O—, —$CONR^3$—, —$NR^3$— (e.g. methylamino), —$NR^3CO$—, —$NR^3CONR^4$—, —$SO_2NR^3$—, —$NR^3SO_2$—, —$NR^3SO_2NR^4$—, —$NR^3C(O)O$—, —$NR^3C(O)OR^4$—, optionally substituted $C_1$-$C_4$ alkylene (e.g. methylene or ethylene) or optionally substituted —$C_2$-$C_4$ alkenylene (e.g. vinyl), and $R^2$ is a 5 or 6 membered heteroaryl, heterocyclyl or aryl ring optionally substituted with one or two substituents independently selected from halogen, cyano, oxo, nitro, —$OR^6$, —$SR^6$, —$NR^6R^7$, —$CONR^6R^7$, —$NR^6COR^7$, —$NR^6CONR^7R^8$, —$COR^6$, —$C(O)OR^6$, —$SO_2R^6$, —$SO_2NR^6R^7$, —$NR^6SO_2R^7$, —$NR^6SO_2NR^7R^8$, —$NR^6C(O)OR^7$, optionally substituted —$C_1$-$C_6$ alkyl, optionally substituted —$C_1$-$C_6$ alkoxy, optionally substituted —C$_2$-C$_6$ alkenyl, optionally substituted —C$_2$-C$_6$ alkynyl, -Q$^2$-R$^6$, -Q$^2$-NR$^6$CONR$^7$R$^8$, -Q$^2$-NR$^6$R$^7$, -Q$^2$-COR$^6$, -Q$^2$-NR$^6$COR$^7$, -Q$^2$-NR$^6$C(O)OR$^7$, -Q$^2$-SO$_2$R$^6$, Q$^2$_CONR$^6$R$^7$, -Q$^2$-CO$_2$R$^6$, -Q$^2$-SO$_2$NR$^6$R$^7$, -Q$^2$-NR$^6$SO$_2$R$^7$ and -Q$^2$-NR$^6$SO$_2$NR$^7$R$^8$, wherein Q$^2$ represents a covalent bond, an oxygen atom, a sulphur atom, —SO—, —SO$_2$—, —CO—, C$_1$-C$_6$ alkylene or optionally substituted C$_2$-C$_6$ alkenylene, and wherein R$^6$, R$^7$, R$^8$ each independently represent hydrogen or optionally substituted C$_1$-C$_6$ alkyl, wherein any alkyl, alkoxy, alkenyl, alkynyl, alkylene or alkenylene is optionally substituted with one or more (e.g. one, two, three or four) substituents selected from halogen, hydroxyl, thiol, cyano, amino, nitro and SF$_5$.

The present invention further relates to compounds of formula (I), or a pharmaceutically acceptable salt thereof, wherein:

R$^{1a}$, R$^{1b}$, R$^{1c}$ and R$^{1d}$ are each hydrogen;

A represents a 5 to 10 membered monocyclic or bicyclic heteroaryl or aryl ring which is unsubstituted or substituted with one or two of -Q$^1$-(R$^2$)$_n$;

each occurrence of -Q$^1$-(R$^2$)$_n$ is the same or different, wherein:

Q$^1$ represents halogen (e.g. fluorine or chlorine), C$_1$-C$_6$ alkyl or C$_1$-C$_3$ alkyl optionally substituted with one or more fluorine, a covalent bond, an oxygen atom, C$_1$-C$_6$ alkylene or C$_1$-C$_3$ alkylene, wherein the alkylene is optionally substituted with one or more substitutents selected from halogen, hydroxyl, thiol, cyano, amino, nitro and SF$_5$;

R$^2$ represents a 5 to 10 membered heterocyclyl, cycloalkyl, heteroaryl or aryl ring, in particular, R$^2$ represents phenyl, pyrazolyl, indazolyl, imidazolyl and thiazolyl.

Examples of the heteroaryl and aryl ring represented by A include those shown below:

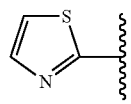 A

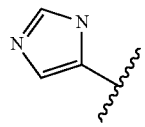 B

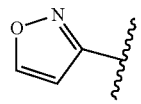 C

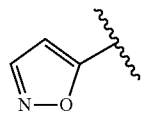 D

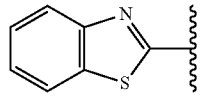 E

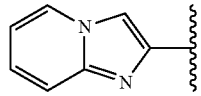 F

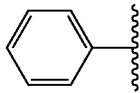 G

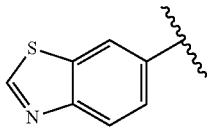 H

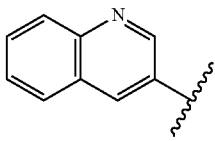 I

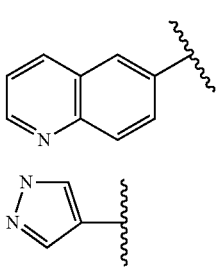 J

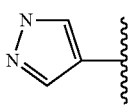 K wherein

represents the point of attachment to the remainder of the molecule, i.e. to the amide nitrogen, and wherein ring A is optionally substituted with one or more of -Q$^1$-(R$^2$)$_n$. Hydrogen atoms attached to the ring nitrogen atoms have not been shown. It will be understood by the skilled person which ring nitrogen atoms are suitable for substitution and where not substituted the nitrogen may be bound to a hydrogen atom to complete its valency, where appropriate.

Examples of novel compounds of formula (I) include:
N-(4-chloro-3-(trifluoromethyl)phenyl)-1-cyano-3-fluoropyrrolidine-3-carboxamide
1-cyano-3-fluoro-N-(4-phenylthiazol-2-yl)pyrrolidine-3-carboxamide
N-(benzo[d]thiazol-6-yl)-1-cyano-3-fluoropyrrolidine-3-carboxamide
1-cyano-3-fluoro-N-(quinolin-3-yl)pyrrolidine-3-carboxamide
1-cyano-3-fluoro-N-(quinolin-6-yl)pyrrolidine-3-carboxamide
1-cyano-3-fluoro-N-(3-(2-methylthiazol-4-yl)phenyl)pyrrolidine-3-carboxamide
1-cyano-3-fluoro-N-(3-phenoxyphenyl)pyrrolidine-3-carboxamide
1-cyano-3-fluoro-N-(5-phenylthiazol-2-yl)pyrrolidine-3-carboxamide
(R)-1-cyano-3-fluoro-N-(5-phenylthiazol-2-yl)pyrrolidine-3-carboxamide
1-cyano-3-fluoro-N-(5-phenylisoxazol-3-yl)pyrrolidine-3-carboxamide 1-cyano-3-fluoro-N-(1-phenyl-1H-imidazol-4-yl)pyrrolidine-3-carboxamide
(S)-1-cyano-3-fluoro-N-(1-phenyl-1H-pyrazol-4-yl)pyrrolidine-3-carboxamide
(R)-1-cyano-3-fluoro-N-(1-phenyl-1H-pyrazol-4-yl)pyrrolidine-3-carboxamide
(R)-1-cyano-N-(1-(4-cyanophenyl)-1H-imidazol-4-yl)-3-fluoropyrrolidine-3-carboxamide
(R)—N-(1-benzyl-1H-pyrazol-4-yl)-1-cyano-3-fluoropyrrolidine-3-carboxamide
N-(6-(1H-pyrazol-4-yl)benzo[d]thiazol-2-yl)-1-cyano-3-fluoropyrrolidine-3-carboxamide
1-cyano-3-fluoro-N-(6-phenylbenzo[d]thiazol-2-yl)pyrrolidine-3-carboxamide
N-(5-(1H-indazol-4-yl)thiazol-2-yl)-1-cyano-3-fluoropyrrolidine-3-carboxamide
(R)—N-(5-(1H-indazol-7-yl)thiazol-2-yl)-1-cyano-3-fluoropyrrolidine-3-carboxamide
1-cyano-3-fluoro-N-(3-phenylisoxazol-5-yl)pyrrolidine-3-carboxamide
(R)-1-cyano-3-fluoro-N-(3-phenylisoxazol-5-yl)pyrrolidine-3-carboxamide
N-(5-(3-carbamoylphenyl)thiazol-2-yl)-1-cyano-3-fluoropyrrolidine-3-carboxamide
1-cyano-3-fluoro-N-(5-(3-(methylcarbamoyl)phenyl)thiazol-2-yl)pyrrolidine-3-carboxamide
(R)-1-cyano-3-fluoro-N-(5-(3-(methylcarbamoyl)phenyl)thiazol-2-yl)pyrrolidine-3-carboxamide
N-(5-(3-(1H-imidazol-1-yl)phenyl)thiazol-2-yl)-1-cyano-3-fluoropyrrolidine-3-carboxamide
N-(3-(3-(1H-imidazol-1-yl)phenyl)isoxazol-5-yl)-1-cyano-3-fluoropyrrolidine-3-carboxamide
(R)—N-(3-(3-(1H-imidazol-1-yl)phenyl)isoxazol-5-yl)-1-cyano-3-fluoropyrrolidine-3-carboxamide
N-(6-(1H-pyrazol-5-yl)imidazo[1,2-a]pyridin-2-yl)-1-cyano-3-fluoropyrrolidine-3-carboxamide
1-cyano-3-fluoro-N-(6-(3-(methylcarbamoyl)phenyl)benzo[d]thiazol-2-yl)pyrrolidine-3-carboxamide
or pharmaceutically acceptable salts thereof.

It should be noted that each of the chemical compounds listed above represents a particular and independent aspect of the invention.

According to a further aspect of the invention there is provided a process for the preparation of a compound of formula (I) or a pharmaceutically acceptable salt thereof comprising the steps of reacting an acid of formula (III) with a compound A-NH$_2$ to form an amide:

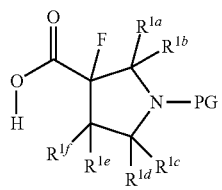

(III)

Where R$^{1a}$-R$^{1f}$ are as defined elsewhere and PG is an amine protecting group. The protecting group may be but is not limited to BOC. It is clear to a person skilled in the art to combine or adjust such a protecting chemical group. After coupling of A-NH$_2$ to form an amide, the protecting group may be removed to leave the free amine according to formula (IV) which can then be treated with cyanogen bromide to form compounds according to formula (I).

According to a further aspect of the invention there is provided a process for the preparation of a compound of formula (I) or a pharmaceutically acceptable salt thereof comprising the steps of reacting an amine of formula (IV) with cyanogen bromide to form N—CN compounds:

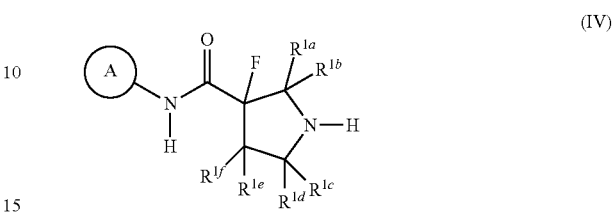

(IV)

Where R$^{1a}$-R$^{1f}$ and A are as defined elsewhere.

According to a further aspect of the invention there is provided a pharmaceutical composition comprising a compound of the invention.

Pharmaceutical compositions of this invention comprise any of the compounds of the invention combined with any pharmaceutically acceptable carrier, adjuvant or vehicle.

Examples of pharmaceutically acceptable carriers, are known to those skilled in the art and include but are not limited to preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may be in the form of, for example, tablets, capsules, powders, granules, elixirs, lozenges, suppositories, syrups and liquid preparations including suspensions and solutions. The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

The compounds of the invention may be used in the treatment of disorders and diseases related to DUB inhibition, particularly Cezanne 1 and USP30 inhibition.

According to a further aspect of the invention there is provided a compound of formula (I) or pharmaceutical composition thereof for use in therapy. In particular, the compounds of the invention have use in the treatment of cancer and more particularly in the treatment of cancers linked to DUB activity. Compounds of the invention may be useful against any DUB enzyme, including but not limited to Cezanne 1 and USP30.

The compounds described herein may be used in the manufacture of a medicament for the treatment of cancer linked to DUB activity.

In a further aspect of the invention there is provided a method of treatment or prevention of cancer linked to Cezanne 1 or USP30 activity, the method comprising administering a pharmaceutically effective amount of a compound of the invention or a pharmaceutical composition thereof to an individual suffering from a cancer linked to Cezanne 1 or USP30 activity.

The compounds or compositions disclosed herein may be used to treat cancer. References to "cancer" or "tumour" include but are not limited to breast, ovarian, prostate, lung, kidney, gastric, colon, testicular, head and neck, pancreas, brain, melanoma, bone or other cancers of tissue organs and cancers of the blood cells such as lymphomas and leukaemias. Particular cancers include lymphoma, multiple myeloma, colorectal cancer, and non-small cell lung carcinoma.

The compounds or compositions disclosed herein may be used to treat additional diseases linked to Cezanne 1 activity.

The compounds of the invention or pharmaceutical compositions thereof as described herein may be combined with one or more additional agents. The compounds may be combined with one or more additional anti-tumour therapeutic agents, for example chemotherapeutic drugs or inhibitors of other regulatory proteins. In one embodiment the one or more anti-tumour therapeutic agent is selected from a PARP (poly ADP ribose polymerase) inhibitor, a BRCA2 inhibitor and an ATM inhibitor. In another embodiment the PARP (poly ADP ribose polymerase) inhibitor is an inhibitory RNA (RNAi) molecule (PARPi). In a further embodiment PARP inhibitors may be selected from one or more of Iniparib (BSI 201), Olaparib (AZD-2281), Rucaparib (AG014699, PF-01367338) and Veliparib (ABT-888), MK-4827, CEP-9722, E7016(GPI-21016), LT-673, MP-124, NMS-P118. In a further embodiment the one or more anti-tumour agent is a chemotherapeutic agent. Chemotherapeutic agents may be selected from olaparib, mitomycin C, cisplatin, carboplatin, oxaliplatin, ionizing radiation (IR), camptothecin, irinotecan, topotecan, temozolomide, taxanes, 5-fluoropyrimidines, gemcitabine, and doxorubicin.

As discussed above, the compounds of the invention may be useful in the treatment of disorders and diseases related to USP30 inhibition. The compounds of the invention may therefore be useful in the treatment of disorders or diseases having a component relating to mitochondiral dysfunction.

Mitochondrial dysfunctions result from defects of the mitochondria, which are specialized compartments present in every cell of the body except red blood cells. When mitochondria fail, less and less energy is generated within the cell and cell injury or even cell death will follow. If this process is repeated throughout the body the life of the subject in whom this is happening is severely compromised. Diseases of the mitochondria appear most often in organs that are very energy demanding such as the brain, heart, liver, skeletal muscles, kidney and the endocrine and respiratory system.

The condition involving mitochondrial dysfunction may be selected from a condition involving a mitophagy defect, a condition involving a mutation in mitochondrial DNA, a condition involving mitochondrial oxidative stress, a condition involving a defect in mitochondrial membrane potential, mitochondrial biogenesis, a condition involving a defect in mitochondrial shape or morphology, and a condition involving a lysosomal storage defect.

In particular, the condition involving mitochondrial dysfunction may be selected from a neurodegenerative disease; multiple sclerosis (MS), mitochondrial myopathy, encephalopathy, lactic acidosis, and stroke-like episodes (MELAS) syndrome; Leber's hereditary optic neuropathy (LHON); cancer; neuropathy, ataxia, retinitis pigmentosa-maternally inherited Leigh syndrome (NARP-MILS); Danon disease; diabetes; diabetic nephropathy; metabolic disorders; heart failure; ischemic heart disease leading to myocardial infarction; psychiatric diseases, for example schizophrenia; multiple sulfatase deficiency (MSD); mucolipidosis II (ML II); mucolipidosis III (ML III); mucolipidosis IV (ML IV); GM1-gangliosidosis (GM1); neuronal ceroid-lipofuscinoses (NCL1); Alpers disease; Barth syndrome; Beta-oxidation defects; carnitine-acyl-carnitine deficiency; carnitine deficiency; creatine deficiency syndromes; co-enzyme Q10 deficiency; complex I deficiency; complex II deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; lethal infantile cardiomyopathy (LIC); Luft disease; glutaric aciduria type II; medium-chain acyl-CoA dehydrogenase deficiency (MCAD); myoclonic epilepsy and ragged-red fiber (MERRF) syndrome; mitochondrial cytopathy; mitochondrial recessive ataxia syndrome; mitochondrial DNA depletion syndrome; myoneurogastointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase (M/SCHAD) deficiency; very long-chain acyl-CoA dehydrogenase (VLCAD) deficiency; and age-dependent decline in cognitive function and muscle strength.

The condition involving mitochondrial dysfunction may be a CNS disorder, for example a neurodegenerative disease. Neurodegenerative diseases include, but are not limited to, Parkinson's disease, Alzheimer's disease, amyotrophic lateral sclerosis (ALS), Huntington's disease, ischemia, stroke, dementia with Lewy bodies, and frontotemporal dementia.

In one embodiment, the condition involving mitochondrial dysfunction is a CNS disorder.

Dosage Forms

The pharmaceutical compositions of the invention may be designed for administration by the oral, parenteral or mucosal route and the choice or the specific form of composition is dependent on the administration route. Thus for oral administration the composition may be in the form, for example, of tablets, lozenges, dragees, films, powders, elixirs, syrups, liquid preparations including dispersions, suspensions, emulsions, solutions or sprays, cachets, granules, capsules, etc. For administration to mucosa the composition may be in the form of sprays, inhalants, dispersions, suspensions, emulsions, solutions, gels, patches, films, ointments, creams, lotions, suppositories etc. For parenteral administration the composition is in the form of a liquid preparation such as a solution, dispersion, emulsion or suspension including liposome compositions.

Preparations according to the invention for parenteral administration include sterile aqueous, aqueous-organic, and organic solutions, suspensions and emulsions.

Such dosage forms are prepared according to techniques known in the art of pharmaceutical formulation. When in the form of sprays or inhalants the pharmaceutical compositions may be administered nasally. Suitable formulations for this purpose are known to those skilled in the art.

The pharmaceutical compositions of the invention may be administered by injection and may be in the form of a sterile liquid preparation for injection, including liposome preparations. The pharmaceutical compositions of the invention may also be in the form of suppositories for rectal administration. These are formulated so that the pharmaceutical composition is solid at room temperature and liquid at body temperature to allow release of the active compound.

The dosages may be varied depending upon the requirements of the patient, the severity of the condition being treated, and the compound being employed. Determination of the proper dosage for a particular situation is within the remit of the person skilled in the skill of the art. Generally, treatment is initiated with smaller dosages which are less than the optimal dose of the compound. Thereafter the dosage is increased by small increments until the optimum effect under the circumstances is reached.

The magnitude of an effective dose of a compound will, of course, vary with the nature of the severity of the condition to be treated and with the particular compound and its route of administration. The selection of appropriate dosages is within the ability of one of ordinary skill in this art, without undue burden. The daily dose range is about 10 µg to about 100 mg per kg body weight of a human and non-human animal and in general may be around 10 µg to 30 mg per kg body weight per dose. The above dose may be given from one to three times per day.

Synthetic Methodologies

Compounds of the invention may be prepared via a variety of synthetic routes. Exemplary routes to certain compounds of the invention are shown below. Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art. Those skilled in the art appreciate that, where appropriate, the individual transformations within a scheme can be completed in a different order. The following schemes describe general synthetic methods whereby intermediate and target compounds of the present invention may be prepared. Additional representative compounds and stereoisomers, racemic mixtures, diastereomers and enantiomers thereof can be synthesized using the intermediates prepared in accordance to the general schemes and other materials, compounds and reagents known to those skilled in the art. All such compounds, stereoisomers, racemic mixtures, diastereomers and enantiomers thereof are intended to be encompassed within the scope of the present invention.

All the compounds were characterised by liquid chromatography-mass spectroscopy (LCMS) and $^1$H NMR.

Synthetic Schemes
Abbreviations
BOC Tert-butoxycarbonyl
br Broad (NMR signal)
d Doublet (NMR signal)
DCM Dichloromethane
DIAD Diisopropyl azodicarboxylate
DIPEA Diisopropylethyl amine
DMAP 4-methylaminopyridine
DMF N,N-Dimethylformamide
DMSO Dimethylsulphoxide
dppf 1,1'-Bis(diphenylphosphino)ferrocene
ES Electrospray
EtOAc Ethyl acetate
h Hour(s)
HATU 1-[Bis(dimethylamino)methylene]-1H-1,2,3-triazolo[4,5-b]pyridinium3-oxid hexafluorophosphate
HBTU 2-(1H-benzotriazol-1-yl)-1,1,3,3-tetramethyluronium hexafluorophosphate
HPLC High performance liquid chromatography
LCMS Liquid chromatography-mass spectrometry
m Multiplet (NMR signal)
MeCN Acetonitrile
MeOH Methanol
Prep Preparative
rt Room temperature
s Singlet (NMR signal)
t Triplet (NMR signal)
TEA Triethylamine
TFA Trifluoroacetic acid
THF Tetrahydrofuran
TLC Thin layer chromatography LCMS Methods

| Method A | |
|---|---|
| Column | XBridge ShieldRP18, 50*2.1 mm 5 µm or equivalent |
| Mobile Phase | (A) 0.05% Ammonia in Water (B) Acetonitrile |
| Flow Rate | 0.8 mL/min |

| Gradient | Time | % B |
|---|---|---|
| | 0.0 | 15 |
| | 0.4 | 15 |
| | 3.4 | 100 |
| | 4.0 | 100 |
| | 4.01 | 15 |

| Method B | |
|---|---|
| Column | Agilent TC-C18, 50 × 2.1 mm, 5 µm |
| Mobile Phase | (A) 0.04% TFA in Water (B) 0.02% TFA in Acetonitrile |
| Flow Rate | 0.8 mL/min |

| Gradient | Time | % B |
|---|---|---|
| | 0 | 0 |
| | 0.4 | 1 |
| | 3.4 | 100 |
| | 4 | 100 |
| Temperature | 50° C. | |

| Method C | |
|---|---|
| Column | BEH C18, 50 × 2.1 mm, 1.7 µm or equivalent |
| Mobile Phase | (A) 5 mM Ammonium Acetate + 0.1% Formic Acid in Water (B) 0.1% Formic Acid in Acetonitrile |
| Flow Rate | 0.55 mL/min |

| Gradient | Time | % B |
|---|---|---|
| | 0.01 | 5 |
| | 0.40 | 5 |
| | 0.80 | 35 |
| | 1.20 | 55 |
| | 2.50 | 100 |
| | 3.30 | 100 |
| | 3.31 | 5 |
| | 4.00 | 5 |

| Method D | |
|---|---|
| Column | BEH C18, 50 × 2.1 mm, 1.7 µm or equivalent |
| Mobile Phase | (A) 5 mM Ammonium Acetate + 0.1% Formic Acid in Water (B) 0.1% Formic Acid in Acetonitrile |
| Flow Rate | 0.45 mL/min |

| Gradient | Time | % B |
|---|---|---|
| | 0.01 | 2 |
| | 0.50 | 2 |
| | 5.00 | 90 |
| | 6.00 | 95 |
| | 7.00 | 95 |
| | 7.01 | 2 |
| | 8.00 | 2 |

Method E

| Column | X-bridge C18, 50 × 4.6 mm, 3.5 µm or equivalent |
|---|---|
| Mobile Phase | (A) 0.1% Ammonia in Water |
|  | (B) 0.1% Ammonia in Acetonitrile |
| Flow Rate | 1.0 mL/min |

| Gradient | Time | % B |
|---|---|---|
|  | 0.01 | 5 |
|  | 5.00 | 90 |
|  | 5.80 | 95 |
|  | 7.20 | 95 |
|  | 7.21 | 5 |
|  | 10.00 | 5 |

Method F

| Column | X-Bridge C18, 50 × 4.6 mm, 3.5 µm or equivalent |
|---|---|
| Mobile Phase | (A) 0.1% Ammonia in Water |
|  | (B) 0.1% Ammonia in Acetonitrile |
| Flow Rate | 1 mL/min |

| Gradient | Time | % B |
|---|---|---|
|  | 0.01 | 0 |
|  | 0.10 | 0 |
|  | 2.50 | 90 |
|  | 2.80 | 95 |
|  | 3.60 | 95 |
|  | 3.61 | 0 |
|  | 5.00 | 0 |

General scheme 1

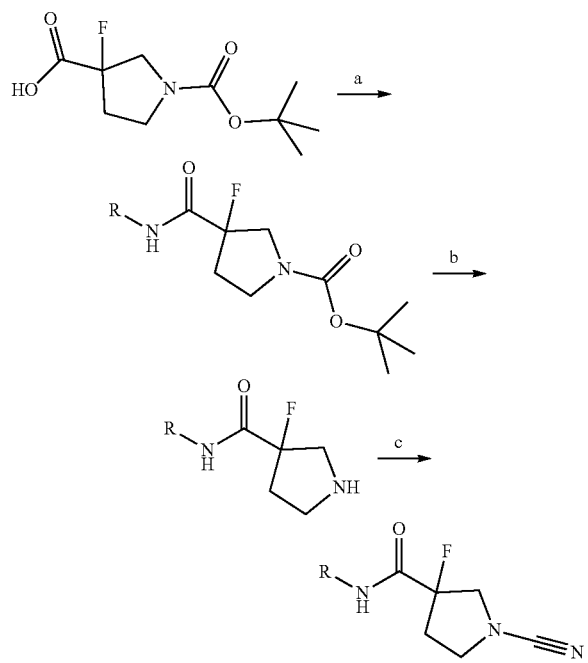

Reagents and conditions: a) HATU or HBTU, DIPEA, DCM or THF, 0° C. then at rt
b) 4M HCl in EtOAc or TFA, EtOAc or DCM, 0° C. then at rt c) cyanogen bromide, NaHCO₃ or K₂CO₃, EtOH or THF, 0° C. then at rt

Example 1 N-(4-chloro-3-(trifluoromethyl)phenyl)-1-cyano-3-fluoropyrrolidine-3-carboxamide (Prepared According to General Scheme 1)

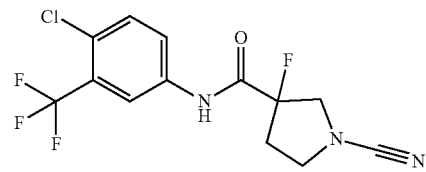 [SMILES: N#CN1CCC(F)(C(=O)Nc2ccc(Cl)c(C(F)(F)F)c2)C1]

Step a.

To a solution of 1-(tert-butoxycarbonyl)-3-fluoropyrrolidine-3-carboxylic acid (made according to WO2013020062 A1) (0.2 mmol) in DCM (1 mL) was added HATU (0.2 mmol). The reaction mixture was stirred at 0° C. for 20 min. The reaction mixture was treated with 4-chloro-3-(trifluoromethyl)aniline (0.2 mmol) and DIPEA (0.6 mmol) and stirred at rt for 16 h. The resulting mixture was concentrated under reduced pressure. The resulting residue was purified by prep-TLC (Petrol Ether/EtOAc=1:2) yielding tert-butyl 3-((4-chloro-3-(trifluoromethyl)phenyl)carbamoyl)-3-fluoropyrrolidine-1-carboxylate. LCMS: Method A, MS: ES+ 411.7.

Step b.

To a solution of tert-butyl 3-((4-chloro-3-(trifluoromethyl)phenyl)carbamoyl)-3-fluoropyrrolidine-1-carboxylate in EtOAc (1 mL) was added HCl/EtOAc (4M, 1 mL). The reaction mixture was stirred at rt for 2 h. The resulting mixture was concentrated under reduced pressure. The residue N-(4-chloro-3-(trifluoromethyl)phenyl)-3-fluoropyrrolidine-3-carboxamide was used for next step directly without further purification. LCMS: Method A, MS: ES+ 311.6.

Step c.

To a solution of N-(4-chloro-3-(trifluoromethyl)phenyl)-3-fluoropyrrolidine-3-carboxamide in EtOH (2 mL) was added cyanogen bromide (0.2 mmol) and NaHCO₃ (0.6 mmol). The reaction mixture was stirred at rt for 16 h. The resulting mixture was concentrated under reduced pressure. The crude was purified by preparative reverse phase HPLC (A: 0.078% CH₃COONH₄ in water, B: MeCN) yielding (2.0 mg, 0.0059 mmol). LCMS: Method A, 2.50 min, MS: ES+ 336.0.

Compounds in Table 1 were synthesised using a procedure similar to that described for Example 1.

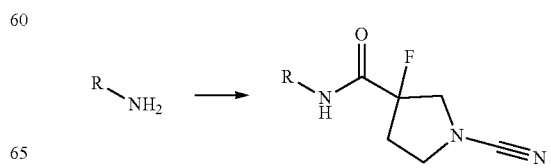

TABLE 1

| Ex | R | Name | LCMS Method | LCMS RT (min) | MS ES+ |
|---|---|---|---|---|---|
| 2 | 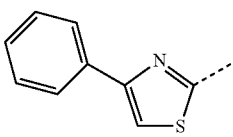 | 1-cyano-3-fluoro-N-(4-phenylthiazol-2-yl)pyrrolidine-3-carboxamide | B | 2.58 | 317.4 |
| 3 | 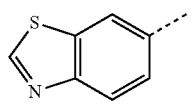 | N-(benzo[d]thiazol-6-yl)-1-cyano-3-fluoropyrrolidine-3-carboxamide | B | 2.30 | 291.3 |
| 4 | 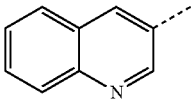 | 1-cyano-3-fluoro-N-(quinolin-3-yl)pyrrolidine-3-carboxamide | B | 2.20 | 285.3 |
| 5 | 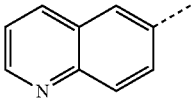 | 1-cyano-3-fluoro-N-(quinolin-6-yl)pyrrolidine-3-carboxamide | B | 1.59 | 285.3 |
| 6 | 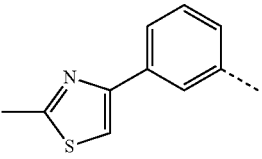 | 1-cyano-3-fluoro-N-(3-(2-methylthiazol-4-yl)phenyl)pyrrolidine-3-carboxamide | B | 2.39 | 331.4 |
| 7 | 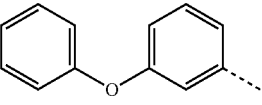 | 1-cyano-3-fluoro-N-(3-phenoxyphenyl)pyrrolidine-3-carboxamide | B | 2.43 | 326.3 |

Example 8 1-cyano-3-fluoro-N-(5-phenylthiazol-2-yl) pyrrolidine-3-carboxamide (Prepared According to General Scheme 1)

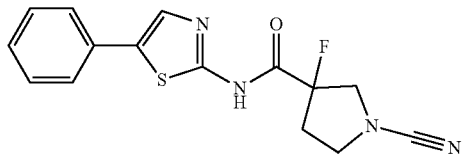 [SMILES: N#CN1CCC(F)(C(=O)Nc2ncc(-c3ccccc3)s2)C1]

Step a.

To a solution of 1-(tert-butoxycarbonyl)-3-fluoropyrrolidine-3-carboxylic acid (0.15 g, 0.64 mmol) in THF (10 ml) was added HBTU (0.48 g, 1.28 mmol) and DIPEA (0.25 g, 1.93 mmol) and stirred for 30 min at rt. The reaction mixture was treated with 5-phenylthiazol-2-amine (0.1 g, 0.58 mmol) and stirred for 18 h. The resulting reaction mixture was poured into NaHCO$_3$ solution (50 ml) and extracted with EtOAc (2×15 ml). The combined organic phase was wash with brine (2×50 ml) and dried over Na$_2$SO$_4$, filtered and concentrated under reduced pressure yielding tert-butyl 3-fluoro-3-((5-phenylthiazol-2-yl)carbamoyl)pyrrolidine-1-carboxylate (0.25 g, 0.64 mmol), This material was used directly for the next step without further purification. LCMS: Method C, 2.38 min, MS: ES+ 336.2 (M-56).

Step b.

To a solution of tert-butyl 3-fluoro-3-((5-phenylthiazol-2-yl)carbamoyl)pyrrolidine-1-carboxylate (0.25 g, 0.64 mmol) in DCM (10 ml) was added TFA (1 ml) at 0° C. The reaction mixture was stirred for 1 h at rt. The resulting reaction mixture was concentrated under reduced pressure to obtained residue which was triturated in diethyl ether/n-pentane (20 ml) and evaporated to yielding 3-fluoro-N-(5-phenylthiazol-2-yl)pyrrolidine-3-carboxamide TFA salt (0.42 g, quantitative) LCMS: Method C, 1.59 min, MS: ES+ 292.18.

Step c.

To a solution 3-fluoro-N-(5-phenylthiazol-2-yl)pyrrolidine-3-carboxamide TFA salt (0.42 g, 1.03 mmol) in THF (10 ml) was added K$_2$CO$_3$ (0.58 g, 4.13 mmol) and cyanogen bromide (0.16 g, 1.55 mmol) at 0° C. The reaction mixture was stirred at rt for 30 min. The resulting mixture was poured into water (50 ml) and extracted with EtOAc (2×15 ml). The combined organic phase was washed with brine and dried over Na$_2$SO$_4$, filtered and concentrated under reduced pressure. The resulting residue was purified by column chromatography (35% EtOAc in hexane) yielding 1-cyano-3-fluoro-N-(5-phenylthiazol-2-yl)pyrrolidine-3-carboxamide (0.05 g, 0.16 mmol), LCMS: Method D, 3.95 min, MS: ES+ 317.2; $^1$H NMR (400 MHz, DMSO-d$_6$) δ ppm 12.81 (S, 1H), 7.99 (s, 1H), 7.65 (d, J=7.2 Hz, 2H), 7.44 (t, J=8 Hz, 2H), 7.33 (t, J=7.2 Hz, 1H), 3.85-4.0 (m, 2H), 3.73-3.77 (m, 1H), 3.57-3.64 (m, 1H), 2.42-2.50 (m, 2H).

Example 9 (R)-1-cyano-3-fluoro-N-(5-phenylthiazol-2-yl) pyrrolidine-3-carboxamide

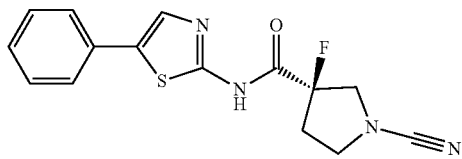 [SMILES: N#CN1CC[C@](F)(C(=O)Nc2ncc(-c3ccccc3)s2)C1]

The title compound was isolated by chiral preparative HPLC of Example 8 to afford the desired enantiomer. LCMS: Method E, 2.54 min, MS: ES+ 317.0; $^1$H NMR (400 MHz, DMSO-d$_6$) δ ppm 12.81 (s, 1H), 7.97 (s, 1H), 7.64 (d, J=8.4 Hz, 2H), 7.43 (t, J=7.6 Hz, 2H), 7.33 (t, J=7.6 Hz, 1H), 3.84-3.99 (m, 2H), 3.72-3.77 (m, 1H), 3.57-3.64 (m, 1H), 2.55-2.67 (m, 1H), 2.39-2.46 (m, 1H).

Example 10 1-cyano-3-fluoro-N-(5-phenylisoxazol-3-yl)pyrrolidine-3-carboxamide

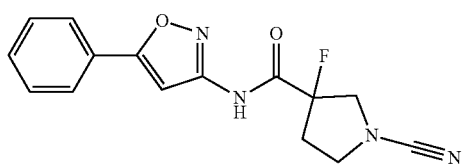 [SMILES: N#CN1CCC(F)(C(=O)Nc2cc(-c3ccccc3)on2)C1]

The title compound was synthesised using a procedure similar to that described for Example 8. LCMS: Method D, 3.97 min, MS: ES+ 301.5; $^1$H NMR (400 MHz, DMSO-d$_6$) δ ppm 11.57 (s, 1H), 7.90-7.92 (m, 2H), 7.52-7.57 (m, 3H), 7.36 (s, 1H), 3.94 (d, J=1.6 Hz, 1H), 3.87 (s, 1H), 3.72-3.78 (m, 1H), 3.57-3.61 (m, 1H), 2.54-2.57 (m, 1H), 2.41-2.45 (m, 1H).

Example 11 1-cyano-3-fluoro-N-(1-phenyl-1H-imidazol-4-yl)pyrrolidine-3-carboxamide

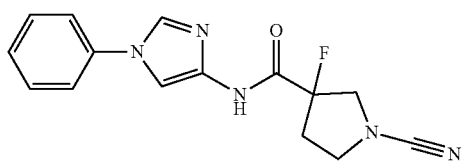 [SMILES: N#CN1CCC(F)(C(=O)Nc2cn(-c3ccccc3)cn2)C1]

Step a.

To a solution of 4-nitroimidazole (5 g, 44.2 mmol) in MeOH (40 ml) was added phenyl boronic acid (8.77 g, 71.66 mmol) at rt and treated with CuCl$_2$ (0.71 g, 5.3 mmol) and NaOH (1.76 g, 44.2 mmol). The reaction mixture was stirred at 80° C. for 16 h whilst continuing the slow purging of O$_2$ gas throughout the reaction time. The resulting reaction mixture was allowed to cool to rt and the purging of O$_2$ gas was removed. The reaction mixture was then concentrated under reduced pressure. The obtained crude material was poured into water (500 ml) and extracted with EtOAc (3×150 ml). The combined organic phase was wash with NaHCO$_3$ solution (200 ml) and dried over Na$_2$SO$_4$, filtered and concentrated under reduced pressure to yield 4-nitro-1-phenyl-1H-imidazole (1.5 g, 7.93 mmol), LCMS: Method C, 1.76 min, MS: ES+ 191.09.

Step b.

To a solution of 4-nitro-1-phenyl-1H-imidazole (0.17 g, 0.89 mmol) in THF (5 ml) was added 10% Pd/C (0.1 g), at rt. The reaction mixture was purged with H$_2$ gas for 2 h at rt. The resulting reaction mixture was carefully filtered through celite hyflow and concentrated under reduced pressure to yield 1-phenyl-1H-imidazol-4-amine, LCMS: Method C, 2.86 min, MS: ES+ 159.93. This material was directly used for the next step without further purification.

Steps c-e.

The title compound was synthesised from the intermediate above using a procedure similar to that described for steps a-c of Example 8. LCMS: Method D, 3.29 min, MS: ES+ 300.3; $^1$H NMR (400 MHz, DMSO-d$_6$) δ ppm 10.89 (s, 1H), 8.19 (s, 1H), 7.79 (s, 1H), 7.65 (d, J=7.6 Hz, 2H), 7.52 (t, J=8.4 Hz, 2H), 7.37 (t, J=7.6 Hz, 1H), 3.94-3.90 (m, 1H), 3.71-3.87 (m, 2H), 3.55-3.62 (m, 1H), 2.38-2.50 (m, 2H).

Example 12 (S)-1-cyano-3-fluoro-N-(1-phenyl-1H-pyrazol-4-yl)pyrrolidine-3-carboxamide

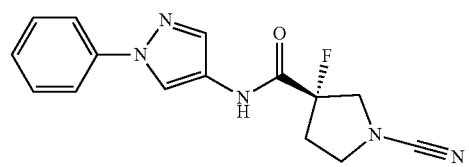 [SMILES: N#CN1CC[C@@](F)(C(=O)Nc2cnn(-c3ccccc3)c2)C1]

The title compound was synthesised according to Example 8 and isolated by chiral preparative HPLC to afford the desired enantiomer. LCMS: Method D, 3.87 min, MS: ES+ 300.0; $^1$H NMR (400 MHz, DMSO-d$_6$) δ ppm 10.81 (s, 1H), 8.62 (s, 1H), 7.90 (s, 1H), 7.81 (d, J=7.6 Hz, 2H), 7.49 (t, J=8.4 Hz, 2H), 7.31 (t, J=7.6 Hz, 1H), 3.94-3.90 (m, 1H), 3.71-3.87 (m, 2H), 3.55-3.62 (m, 1H), 2.38-2.50 (m, 2H).

Example 13 (R)-1-cyano-3-fluoro-N-(1-phenyl-1H-pyrazol-4-yl)pyrrolidine-3-carboxamide

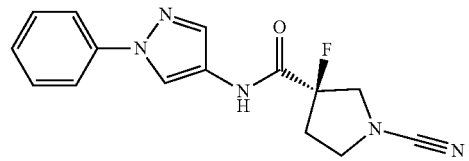 [SMILES: N#CN1CC[C@](F)(C(=O)Nc2cnn(-c3ccccc3)c2)C1]

The title compound was synthesised according to Example 8 and isolated by chiral preparative HPLC to afford the desired enantiomer. LCMS: Method D, 3.87 min, MS: ES+ 300.0; $^1$H NMR (400 MHz, DMSO-d$_6$) δ ppm 10.81 (s, 1H), 8.62 (s, 1H), 7.90 (s, 1H), 7.80 (d, J=7.6 Hz, 2H), 7.50 (t, J=8.4 Hz, 2H), 7.31 (t, J=7.6 Hz, 1H), 3.94-3.90 (m, 1H), 3.71-3.87 (m, 2H), 3.55-3.62 (m, 1H), 2.38-2.50 (m, 2H).

Example 14 (R)-1-cyano-N-(1-(4-cyanophenyl)-1H-imidazol-4-yl)-3-fluoropyrrolidine-3-carboxamide

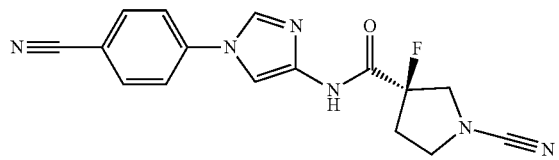 [SMILES: N#Cc1ccc(-n2cnc(NC(=O)[C@@]3(F)CCN(C#N)C3)c2)cc1]

The title compound was synthesised using a procedure similar to that described for Example 11 and the single enantiomer separated by chiral prep. HPLC. LCMS: Method D, 3.32 min, MS: ES+ 325.5; $^1$H NMR (400 MHz, DMSO-d$_6$) δ ppm 10.98 (s, 1H), 8.40 (d, J=1.6 Hz, 1H), 8.00-8.02 (m, 2H), 7.91-7.94 (m, 3H), 3.91 (s, 1H), 3.83 (s, 1H), 3.71-3.74 (m, 1H), 3.58-3.62 (m, 1H), 2.57-2.59 (m, 1H), 2.42-2.45 (m, 1H).

Example 15 (R)—N-(1-benzyl-1H-pyrazol-4-yl)-1-cyano-3-fluoropyrrolidine-3-carboxamide

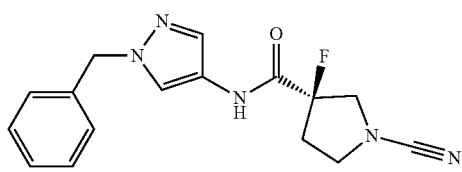 [SMILES: N#CN1CC[C@](F)(C(=O)Nc2cnn(Cc3ccccc3)c2)C1]

The title compound was synthesised according to Example 8 and isolated by chiral preparative HPLC to afford the desired enantiomer. LCMS: Method F, 5.48 min, MS: ES+ 314.1; $^1$H NMR (400 MHz, DMSO-d$_6$) δ ppm 10.59 (s, 1H), 8.06 (s, 1H), 7.60 (s, 1H), 7.36-7.20 (m, 5H), 5.30 (s, 2H), 3.86-3.55 (m, 4H), 2.57-2.33 (m, 2H).

Example 16 N-(6-(1H-pyrazol-4-yl)benzo[d]thiazol-2-yl)-1-cyano-3-fluoropyrrolidine-3-carboxamide

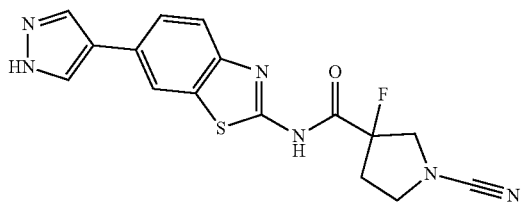 [SMILES: N#CN1CCC(F)(C(=O)Nc2nc3ccc(-c4cn[nH]c4)cc3s2)C1]

Step a.

To a stirred solution of 2-amino-6-bromobenzothiazole (0.3 g, 1.31 mmol) and pyrazole-4-boronic acid pinacol ester (0.63 g, 3.27 mmol) in DMF: water (10:3, 13 ml) was added CsF (0.63 g, 4.19 mmol) at rt in a microwave tube. The reaction mixture was degassed for 15 min at rt. Pd(PPh$_3$)$_2$Cl$_2$ (0.14 g, 0.20 mmol) was added to the reaction mixture at rt. The reaction mixture was heated at 140° C. for 1 h in microwave. The resulting reaction mixture was allowed to cool at rt, poured into a solution of water: EtOAc (1:1, 60 ml) and filtered through celite bed. The organic phase was separated and the aqueous phase was re-extracted using EtOAc (30 ml) and 10% MeOH in DCM (2×30 ml). The combined organic phase was separated, dried over Na$_2$SO$_4$, filtered and concentrated under reduced pressure. The resulting residue was purified by flash chromatography (0-10% EtOAc in hexane, 5% MeOH in DCM) yielding 6-(1H-pyrazol-4-yl)benzo[d]thiazol-2-amine (0.22 g, 1.018 mmol). LCMS: Method C, 1.473 min, MS: ES+ 217.11; $^1$H NMR (400 MHz, DMSO-d6) δ ppm: 12.86 (s, 1H), 8.12 (s, 1H), 7.90 (s, 2H), 7.43-7.47 (m, 3H), 7.29 (d, J=8.4 Hz, 1H).

Steps b-d.

The title compound was synthesised from the intermediate above using a procedure similar to that described for steps a-c of Example 8. LCMS: Method D, 3.26 min, MS: ES+ 357.5; $^1$H NMR (400 MHz, DMSO-d$_6$) δ ppm 12.96 (s, 2H), 8.25 (s 1H), 8.14 (br, s, 2H), 7.73 (s, 2H), 3.86-4.02 (m, 2H), 3.73-3.77 (m, 1H), 3.58-3.64 (m, 1H), 2.46-2.48 (m, 2H).

Example 17 1-cyano-3-fluoro-N-(6-phenylbenzo[d]thiazol-2-yl)pyrrolidine-3-carboxamide

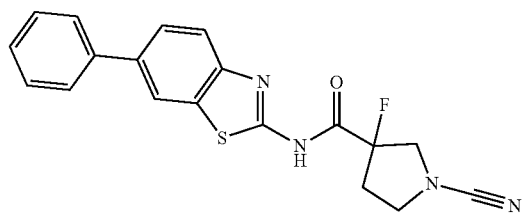 [SMILES: N#CN1CCC(F)(C(=O)Nc2nc3ccc(-c4ccccc4)cc3s2)C1]

The title compound was synthesised using a procedure similar to that described for Example 16 using phenylboronic acid. LCMS: Method F, 5.96 min, MS: ES+ 367.1; $^1$H NMR (400 MHz, DMSO-d$_6$) δ ppm 12.98 (s, 1H), 8.37 (s, 1H), 7.86 (s, 1H), 7.74-7.80 (m, 3H), 7.49 (t, J=7.6 Hz, 2H), 7.38 (t, J=7.2 Hz, 1H), 3.91-4.03 (m, 2H), 3.74-3.79 (m, 1H), 3.59-3.65 (m, 1H), 2.59-2.62 (m, 2H).

Example 18 N-(5-(1H-indazol-4-yl) thiazol-2-yl)-1-cyano-3-fluoropyrrolidine-3-carboxamide

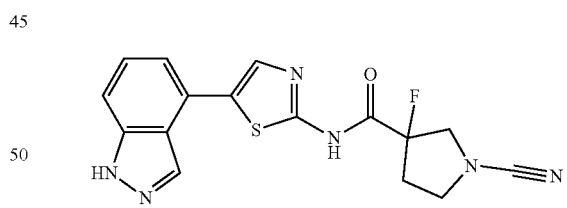

Step a.

To a solution of 4-bromoindazole (1.0 g, 5.07 mmol) in DCM (20 ml) was added TEA (0.85 ml, 6.1 mmol) and DMAP (0.062 g, 0.50 mmol) at rt. Boc anhydride (1.28 ml, 5.58 mmol) was added drop wise to the reaction mixture at rt. The reaction mixture was stirred at rt for 2.5 h. The resulting reaction mixture was poured in to water (30 ml) and extracted with DCM (2×30 ml). The combined organic phase was dried over Na$_2$SO$_4$, filtered and concentrated under reduced pressure. The resulting residue was purified by flash chromatography (15-20% EtOAc in hexane) yielding tert-butyl 4-bromo-1H-indazole-1-carboxylate (1.5 g, 5.06 mmol). LCMS: Method C, 2.601 min, MS: ES+ 297.19; $^1$H NMR (400 MHz, DMSO-d6) δ ppm: 8.20 (s, 1H), 8.15 (d, J=8.0 Hz, 1H), 7.47 (dd, J=0.8 Hz, 7.6 Hz, 1H), 7.37-7.41 (m, 1H), 1.74 (s, 9H).

Step b.

To a stirred solution of tert-butyl 4-bromo-1H-indazole-1-carboxylate (0.3 g, 1.01 mmol) and tert-butyl (4-methoxybenzyl)(5-(4,4,5,5-tetramethyl-1,3,2-dioxaborolan-2-yl)thiazol-2-yl)carbamate (0.67 g, 1.515 mmol) in toluene:water (9:1, 10 ml) was added Na₂CO₃ (0.21 g, 2.02 mmol) at rt. The reaction mixture was degassed for 20 min at rt. Pd(dppf)Cl₂ (0.074 g, 0.101 mmol) was added to the reaction mixture at rt. The reaction mixture was heated at 105° C. for 1 h. The resulting reaction mixture was allowed to cool at rt, poured into water (20 ml) and extracted with EtOAc (2×20 ml). The combined organic phase was separated, dried over Na₂SO₄, filtered and concentrated under reduced pressure. The resulting residue was purified by flash chromatography (7-20% EtOAc in hexane) yielding tert-butyl 4-(2-((tert-butoxycarbonyl)(4-methoxybenzyl)amino)thiazol-5-yl)-1H-indazole-1-carboxylate (0.44 g, 0.819 mmol). LCMS: Method C, 3.27 min, MS: ES+ 537.53.

Step c.

A solution of tert-butyl 4-(2-((tert-butoxycarbonyl)(4-methoxybenzyl)amino)thiazol-5-yl)-1H-indazole-1-carboxylate (0.42 g, 0.78 mmol) in TFA (10 ml) was heated to 85° C. for 3 h. The reaction mixture was allowed to cool at rt and excess of TFA was distilled under vacuum. The resulting reaction mixture was poured into a solution of water: EtOAc (1:1, 40 ml) and basified using solid NaHCO₃. The organic layer was separated and aqueous layer was re-extracted with EtOAc (2×20 ml). The combined organic phase was separated, dried over Na₂SO₄, filtered and concentrated under reduced pressure. The resulting residue was purified by solvent trituration using DCM (5 ml) to yielding 5-(1H-indazol-4-yl)thiazol-2-amine (0.11 g, mmol). LCMS: Method C, 1.41 min, MS: ES+ 217.11; ¹H NMR (400 MHz, DMSO-d6) δ ppm: 13.22 (s, 1 H), 8.32 (s, 1 H), 7.61 (s, 1 H), 7.38 (d, J=8.4 Hz, 1 H), 7.28-7.32 (m, 1H), 7.26 (s, 2H), 7.07 (d, J=7.2 Hz, 1H).

Steps d-f.

The title compound was synthesised from the intermediate above using a procedure similar to that described for steps a-c of Example 8. LCMS: Method E, 2.26 min, MS: ES+ 357.0; ¹H NMR (400 MHz, DMSO-d₆) δ ppm 13.37 (s, 1H), 12.88 (s, 1H), 8.41 (s, 1H), 8.16 (s, 1H), 7.55 (d, J=8.4 Hz, 1H), 7.41 (t, J=8.0 Hz, 1H), 7.34 (d, J=6.8 Hz, 1H), 3.96-4.02 (m, 1H), 3.91 (s, 1H), 3.74-3.79 (m, 1H), 3.59-3.66 (m, 1H), 2.56-2.62 (m, 2H).

Example 19 (R)—N-(5-(1H-indazol-7-yl)thiazol-2-yl)-1-cyano-3-fluoropyrrolidine-3-carboxamide

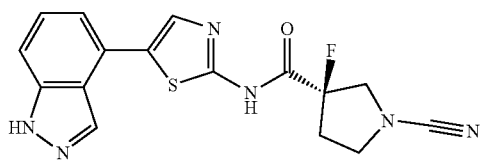 [SMILES: N#CN1CC[C@](F)(C(=O)Nc2ncc(-c3cccc4[nH]ncc34)s2)C1]

Step a.

To a stirred solution of 1H-indazole-7-boronic acid (0.50 g, 3.09 mmol) and tert-butyl (5-bromothiazol-2-yl)(4-methoxybenzyl)carbamate (0.74 g, 1.85 mmol) in toluene:water (9:1, 20 ml) was added Na₂CO₃ (0.654 g, 6.17 mmol) at rt. The reaction mixture was degassed for 30 min at rt and then treated with Pd(dppf)Cl₂ (0.22 g, 0.308 mmol). The reaction mixture was heated at 110° C. for 2 h. The resulting reaction mixture was allowed to cool to rt, poured into water (30 ml) and extracted with EtOAc (2×30 ml). The combined organic phase was separated, dried over Na₂SO₄, filtered and concentrated under reduced pressure. The resulting residue was purified by flash chromatography (22% EtOAc in hexane) yielding tert-butyl (5-(1H-indazol-7-yl)thiazol-2-yl)(4-methoxybenzyl)carbamate (0.575 g, 1.32 mmol). LCMS: Method C, 2.67 min, MS: ES+ 437.5; ¹H NMR (400 MHz, DMSO-d6) δ ppm: 13.26 (s, 1H), 8.21-8.23 (m, 1H), 8.03 (s, 1H), 7.76 (d, J=8.0 Hz, 1H), 7.46 (d, J=7.2 Hz, 1H), 7.29 (d, J=8.4 Hz, 2H), 7.18 (t, J=7.6 Hz, 1H), 6.92 (d, J=8.8 Hz, 2H), 5.24 (s, 2H), 3.73 (s, 3H), 1.50 (s, 9H).

Step b.

A solution of tert-butyl (5-(1H-indazol-7-yl)thiazol-2-yl)(4-methoxybenzyl)carbamate (0.57 g, 1.30 mmol) in TFA (11.5 ml) was heated to 80° C. for 5 h. The resulting reaction mixture was allowed to cool to rt, poured into a solution of water: EtOAc (1:1, 60 ml) and basified using solid NaHCO₃. The organic layer was separated and aqueous layer was re-extracted with EtOAc (30 ml). The combined organic phase was separated, dried over Na₂SO₄, filtered and concentrated under reduced pressure. The resulting residue was purified by solvent trituration using diethyl ether (2×10 ml) to 5-(1H-indazol-7-yl)thiazol-2-amine (0.274 g, 1.27 mmol). LCMS: Method C, 1.61 min, MS: ES+ 217.14; H NMR (400 MHz, DMSO-d6) δ ppm: 13.11 (s, 1H), 8.16 (s, 1H), 7.62-7.65 (m, 2H), 7.27 (s, 2H), 7.21 (d, J=7.2 Hz, 1H), 7.11 (t, J=7.2 Hz, 1H).

Steps c-e.

The title compound was synthesised from the intermediate above using a procedure similar to that described for steps a-c of Example 8. LCMS: Method D, 3.56 min, MS: ES+ 357.3; ¹H NMR (400 MHz, DMSO-d6) δ ppm 13.87 (br, s, 1H), 13.25 (s, 1H), 8.22 (s, 1H), 8.09 (s, 1H), 7.75 (d, J=7.6 Hz, 1H), 7.46 (s, 1H), 7.16-7.20 (m, 1H), 3.98-4.01 (m, 1H), 3.85-3.93 (m, 1H), 3.73-3.77 (m, 1H), 3.57-3.64 (m, 1H), 2.56-2.59 (m, 2H).

Example 20 1-cyano-3-fluoro-N-(3-phenylisoxazol-5-yl)pyrrolidine-3-carboxamide

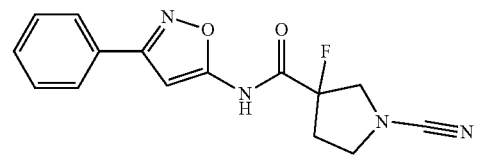 [SMILES: N#CN1CCC(F)(C(=O)Nc2cc(-c3ccccc3)no2)C1]

Step a.

To a solution of 3-phenylisoxazol-5-amine (0.137 g, 0.85 mmol) (CAS No: 4369-55-5, available from TCI India) and 1-(tert-butoxycarbonyl)-3-fluoropyrrolidine-3-carboxylic acid (0.2 g, 0.8536 mmol) in DCM (10 ml) was added pyridine (0.8 ml, 9.44 mmol) at 0° C. Phosphorous oxychloride (0.8 ml, 8.536 mmol) was added drop wise in to the reaction mixture at 0° C. The reaction mixture was stirred at rt for 30 min. The resulting reaction mixture was poured into 10% citric acid solution (100 ml) and extracted with DCM (3×50 ml). The combined organic phase was collected, dried over Na₂SO₄, filtered and concentrated under reduced pressure yielding tert-butyl 3-fluoro-3-((3-phenylisoxazol-5-yl)carbamoyl)pyrrolidine-1-carboxylate (0.33 g, quantitative). LCMS: Method C, 2.52 min, MS: ES− 374.6.

Steps b-c.

The title compound was synthesised from the intermediate above using a procedure similar to that described for steps b-c of Example 8. LCMS: Method E, 2.42 min, MS: ES+ 300.9; $^1$H NMR (400 MHz, DMSO-d$_6$) δ ppm 12.28 (s, 1H), 7.86-7.89 (m, 2H), 7.51 (t, J=3.2 Hz, 3H), 6.88 (s, 1H), 3.84-3.97 (m, 2H), 3.73-3.78 (m, 1H), 3.58-3.65 (m, 1H), 2.33-2.47 (m, 2H).

Example 21 (R)-1-cyano-3-fluoro-N-(3-phenylisoxazol-5-yl)pyrrolidine-3-carboxamide

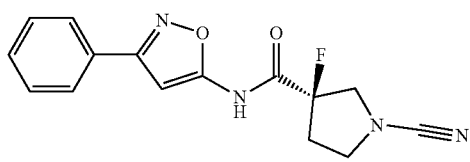 [SMILES: N#CN1CC[C@](F)(C(=O)Nc2cc(-c3ccccc3)no2)C1]

The title compound was isolated by chiral preparative HPLC of Example 20 to afford the desired enantiomer. LCMS: Method E, 2.36 min, MS: ES+ 300.9; $^1$H NMR (400 MHz, DMSO-d$_6$) δ ppm 12.28 (s, 1H), 7.86-7.88 (m, 2H), 7.50-7.54 (m, 3H), 6.86 (s, 1H), 3.86-3.97 (m, 2H), 3.72-3.78 (m, 1H), 3.57-3.64 (m, 1H), 2.53-2.67 (m, 1H), 2.38-2.47 (m, 1H).

Example 22 N-(5-(3-carbamoylphenyl)thiazol-2-yl)-1-cyano-3-fluoropyrrolidine-3-carboxamide

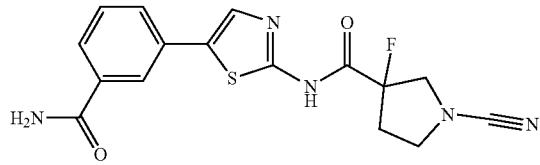 [SMILES: N#CN1CCC(F)(C(=O)Nc2ncc(-c3cccc(C(N)=O)c3)s2)C1]

Step a.

To a solution of thiazol-2-amine (5 g, 49.9 mmol) in toluene (150 ml) was added 2,4-dimethoxybenzaldehyde (9.13 g, 54.9 mmol) and acetic acid (0.1 ml) at rt. The reaction mixture was heated at 130° C. for 20 h. The reaction mixture was concentrated under vacuum to remove toluene. The obtained residue was diluted with ethanol (75 ml) and DCM (75 ml). NaBH$_4$ (3.02 g, 79.84 mmol) was added to the reaction mixture at 0° C. The reaction mixture was stirred at rt for 20 h. The resulting reaction mixture was poured into water (300 ml) and extracted with DCM (3×150 ml). The combined organic phase was wash with brine solution (150 ml), dried over Na$_2$SO$_4$, filtered and concentrated under reduced pressure. The resulting residue was purified by flash chromatography (30% EtOAc in hexane) yielding N-(2,4-dimethoxybenzyl)thiazol-2-amine (7 g, 28 mmol). MS: ES+ 251.32.

Step b.

To a solution of N-(2,4-dimethoxybenzyl)thiazol-2-amine (0.75 g, 2.99 mmol) in DMA (15 ml) were added 3-bromobenzamide (0.66 g, 3.29 mmol) and potassium acetate (0.74 g, 7.49 mmol). Degassed the reaction mixture for 15 min under N$_2$. Tetrakis(triphenylphosphine)palladium(0) (0.173 g, 0.14 mmol) was added in to reaction mixture and heated at 160° C. for 4 h in microwave. The resulting reaction mixture was poured into water (200 ml) and extracted with ethyl acetate (3×100 ml). The combined organic phase was wash with brine solution (100 ml), dried over Na$_2$SO$_4$, filtered and concentrated under reduced pressure. The residue was triturated with the diethyl ether (20 ml) and dried under vacuum to yielding 3-(2-((2,4-dimethoxybenzyl)amino)thiazol-5-yl)benzamide (0.66 g, 1.78 mmol). MS: ES+ 370.15.

Step c.

To a solution of 3-(2-((2,4-dimethoxybenzyl)amino)thiazol-5-yl)benzamide (0.66 g, 1.78 mmol) in DCM (20 ml) was added TFA (10 ml) at rt. The reaction mixture was stirred at rt for 4 h. The resulting reaction mixture was concentrated under reduced pressure. The obtained residue was diluted with ethyl acetate (100 ml) and wash with NaHCO$_3$ solution (3×100 ml), brine (100 ml) and dried over Na$_2$SO$_4$, filtered and concentrated under reduced pressure to yielding 3-(2-aminothiazol-5-yl)benzamide (0.2 g, 0.91 mmol). MS: ES+ 220.19.

Steps b-d.

The title compound was synthesised from the intermediate above using a procedure similar to that described for steps a-c of Example 8. LCMS: Method E, 2.06 min, MS: ES+ 359.9; $^1$H NMR (400 MHz, DMSO-d$_6$) δ ppm 12.84 (s, 1H), 8.11-8.13 (m, 2H), 8.05 (s, 1H), 7.80-7.82 (m, 2H), 7.49-7.53 (m, 2H), 3.89-4.00 (m, 2H), 3.73-3.77 (m, 1H), 3.58-3.64 (m, 1H), 2.45-2.50 (m, 2H).

Example 23 1-cyano-3-fluoro-N-(5-(3-(methylcarbamoyl)phenyl) thiazol-2-yl)pyrrolidine-3-carboxamide

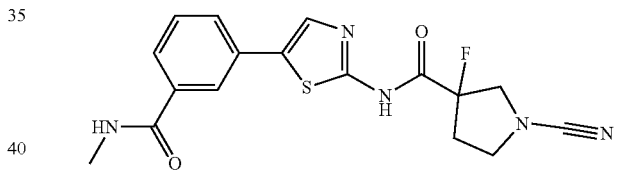

Step a.

A suspension of 2-amino-5-bromothiazole hydrobromide (30.0 g, 116.35 mmol) and TEA (24.1 ml, 174.53 mmol) in THF (350 ml) was stirred at rt for 6 h. The resulting precipitate was removed by filtration and the filtrate was concentrated under reduced pressure yielding 2-amino-5-bromothiazole (17 g, 94.97 mmol). This material was immediately used for the next step without further purification.

Step b.

To a solution of 2-amino-5-bromothiazole (13 g, 72.62 mmol) and DMAP (0.44 g, 3.63 mmol) in THF (130 ml) was added (Boc)$_2$O (15.83 g, 72.62 mmol) at rt. The reaction mixture was stirred at rt for 6 h. Excess THF was removed under reduced pressure and the resulting residue was purified by column chromatography (0-5% EtOAc in Hexane) yielding tert-butyl (5-bromothiazol-2-yl)carbamate (14.5 g, 52.16 mmol). LCMS: Method C, 2.28 min, MS: ES+ 279.08; $^1$H NMR (400 MHz, DMSO-d$_6$) δ ppm 11.75 (s, 1H), 7.44 (s, 1H), 1.48 (s, 9H).

Step c.

A mixture of tert-butyl (5-bromothiazol-2-yl)carbamate (1.0 g, 3.60 mmol), triphenylphosphine (2.07 g, 7.91 mmol) and p-methoxybenzyl alcohol (0.99 g, 7.19 mmol) in THF (10 ml) was cooled at 0° C. DIAD (1.54 ml, 7.91 mmol) was added drop wise to the reaction mixture at 0° C. The reaction mixture was stirred at 0° C. for 10 min and then at rt for 2 h. The resulting reaction mixture was concentrated under reduced pressure and purified by flash chromatography (0-5% EtOAc in Hexane) yielding tert-butyl (5-bromothiazol-2-yl)(4-methoxybenzyl)carbamate (1.1 g, 2.76 mmol). LCMS: Method C, 3.02 min, MS: ES-56 343.1; $^1$H NMR (400 MHz, DMSO-d$_6$) δ ppm 7.57 (s, 1H), 7.22 (d, J=8.4 Hz, 2H), 6.89 (d, J=8.4 Hz, 2H), 5.13 (s, 2H), 3.74 (s, 3H), 1.50 (s, 9H).

Step d.

A solution of tert-butyl (5-bromothiazol-2-yl)(4-methoxybenzyl)carbamate (1.05 g, 2.638 mmol) in dry THF (15 ml) was cooled at –78° C. 2.4M n-BuLi in Hexane (1.07 ml, 2.638 mmol) was added drop wise to the reaction mixture at –78° C. The reaction mixture was stirred at –78° C. for 20 min. 4,4,5,5-tetramethyl-1,3,2-dioxaborolane (0.46 ml, 3.120 mmol) was added to the reaction mixture stirred for a further 30 min. The resulting reaction mixture was allowed to warm to 0° C. and quenched by addition of saturated ammonium chloride solution (100 ml). The resulting mixture was extracted with EtOAc (2×100 ml). The combined organic phase was dried over Na$_2$SO$_4$, filtered and concentrated under reduced pressure yielding tert-butyl (4-methoxybenzyl)(5-(4,4,5,5-tetramethyl-1,3,2-dioxaborolan-2-yl)thiazol-2-yl)carbamate (1.3 g, quantitative yield). This material was directly used for the next step without any purification.

Step e.

A solution of 3-bromobenzoic acid (2.0 g, 9.95 mmol) in THF (40 ml) were added HATU (5.60 g, 14.92 mmol) and DIPEA (3.40 ml, 19.90 mmol) at 0° C. The reaction mixture was stirred for 30 min at rt. Methylamine (2M in THF) (9.90 ml, 19.90 mmol) was added to the reaction mixture at rt and stirred for 18 h. The resulting reaction mixture was combined with one other batch on the same scale prepared by an identical method and poured into saturated NaHCO$_3$ solution (100 ml). The resulting mixture was extracted with EtOAc (2×100 ml). The combined organic phase was dried over Na$_2$SO$_4$, filtered and concentrated under reduced pressure. The resulting residue was purified by flash chromatography (2-3% Methanol in DCM) yielding 3-bromo-N-methylbenzamide (4.13 g, 19.29 mmol). LCMS: Method C, 1.766 min, MS: ES+ 214.14.

Step f.

A suspension of 3-bromo-N-methylbenzamide (0.40 g, 1.87 mmol), tert-butyl (4-methoxybenzyl)(5-(4,4,5,5-tetramethyl-1,3,2-dioxaborolan-2-yl)thiazol-2-yl)carbamate (0.84 g, 1.87 mmol) and Na$_2$CO$_3$ (0.40 g, 3.74 mmol) in toluene: water (9:1) (15 ml) was degassed with nitrogen for 20 min at rt. Pd(dppf)Cl$_2$ (0.14 g, 0.186 mmol) was added in to the reaction mixture at rt. The reaction mixture was heated at 105° C. for 2 h. The resulting reaction mixture was cooled to rt, poured into water (60 ml) and extracted with EtOAc (2×50 ml). The combined organic phase was dried over Na$_2$SO$_4$, filtered and concentrated under reduced pressure. The resulting residue was purified by flash chromatography (60% EtOAc in hexane) yielding tert-butyl (4-methoxybenzyl)(5-(3-(methylcarbamoyl)phenyl)thiazol-2-yl)carbamate (0.36 g, 0.79 mmol). LCMS: Method C, 2.66 min, MS: ES+ 454.55.

Step g.

A solution of tert-butyl (4-methoxybenzyl)(5-(3-(methylcarbamoyl)phenyl)thiazol-2-yl)carbamate (0.34 g, 0.750 mmol) in TFA (6.8 ml) was heated at 75° C. for 6 h. The resulting reaction mixture was concentrated under reduced pressure and saturated NaHCO$_3$ solution (50 ml) was added in to resulting residue. The resulting mixture was extracted with EtOAc (3×50 ml). The combined organic phase was dried over Na$_2$SO$_4$, filtered and concentrated under reduced pressure. The obtained residue was triturated with n-hexane (2×5 ml) yielding 3-(2-aminothiazol-5-yl)-N-methylbenzamide (0.20 g, quantitative). This material was used for the next step without further purification. LCMS: Method C, 1.38 min, MS: ES+ 234.25.

Steps h-j.

The title compound was synthesised from the intermediate above using a procedure similar to that described for steps a-c of Example 8. LCMS: Method D, 3.27 min, MS: ES+ 374.5; $^1$H NMR (400 MHz, DMSO-d$_6$) δ ppm 12.82 (br s, 1H), 8.60-8.59 (m, 1H), 8.06-8.05 (m, 2H), 7.82-7.79 (m, 2H), 7.52 (t, J=7.6, 1H), 3.89-4.00 (m, 2H), 3.73-3.78 (m, 1H), 3.58-3.64 (m, 1H), 2.81 (d, J=4.4, 3H), 2.45-2.52 (m, 2H).

Example 24 (R)-1-cyano-3-fluoro-N-(5-(3-(methylcarbamoyl)phenyl)thiazol-2-yl)pyrrolidine-3-carboxamide

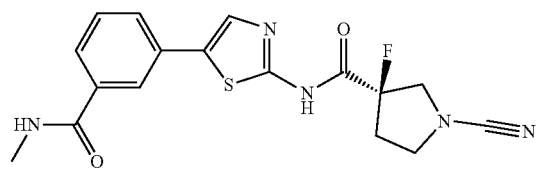 [SMILES: CNC(=O)c1cccc(-c2cnc(NC(=O)[C@@]3(F)CCN(C#N)C3)s2)c1]

The title compound was isolated by chiral preparative HPLC of Example 23 to afford the desired enantiomer. LCMS: Method D, 3.27 min, MS: ES+ 374.5; $^1$H NMR (400 MHz, DMSO-d6) δ ppm 12.84 (br s, 1H), 8.59-8.60 (m, 1H), 8.06-8.05 (m, 2H), 7.80-7.70 (m, 2H), 7.52 (t, J=7.6, 1H), 3.89-4.00 (m, 2H), 3.73-3.78 (m, 1H), 3.58-3.64 (m, 1H), 2.81 (d, J=4.4, 3H), 2.45-2.52 (m, 2H).

Example 25 N-(5-(3-(1H-imidazol-1-yl)phenyl)thiazol-2-yl)-1-cyano-3-fluoropyrrolidine-3-carboxamide

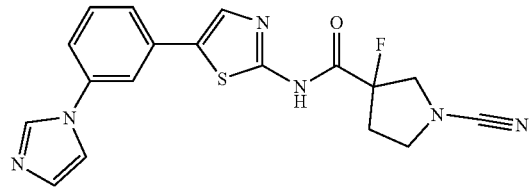 [SMILES: N#CN1CCC(F)(C(=O)Nc2ncc(-c3cccc(-n4ccnc4)c3)s2)C1]

Step a.

A suspension of 1,3-dibromobenzene (2.0 g, 8.48 mmol) in DMSO (7.8 ml) was added 1H-imidazole (0.58 g, 8.48 mmol) and K$_2$CO$_3$ (2.34 g, 16.96 mmol). The reaction mixture was degassed with nitrogen for 10 min at rt. CuI (0.002 g) was added at rt and the reaction mixture was heated at 160° C. for 1 h in microwave. The resulting reaction mixture was poured into water (20 ml) and extracted with EtOAc (5×10 ml). The combined organic phase was collected, dried over Na$_2$SO$_4$, filtered and concentrated under reduced pressure yielding 1-(3-bromophenyl)-1H-imidazole (1.0 g, 4.48 mmol). LCMS: Method C, 1.53 min, MS: ES+ 223.1.

Step b.

A solution of 1-(3-bromophenyl)-1H-imidazole (0.25 g, 1.12 mmol) and tert-butyl (4-methoxybenzyl)(5-(4,4,5,5-tetramethyl-1,3,2-dioxaborolan-2-yl)thiazol-2-yl)carbamate (1.00 g, 2.24 mmol) in toluene was degassed with nitrogen for 15 min at rt. NH$_4$OH (0.08 g, 2.24 mmol) and Pd(dppf)Cl$_2$ (0.08 g, 0.11 mmol) were added to the reaction mixture at rt. The resulting reaction mixture was stirred at rt for 2 h and then heated at 80° C. for 2 h. The resulting reaction mixture was cooled to rt, poured into water (100 ml) and extracted with EtOAc (2×100 ml). The combined organic phase was washed with brine solution (75 ml), dried over Na$_2$SO$_4$, filtered and concentrated under reduced pressure. The resulting residue was purified by flash chromatography (12.6% EtOAc in hexane) yielding tert-butyl (5-(3-(1H-imidazol-1-yl)phenyl)thiazol-2-yl)(4-methoxybenzyl)carbamate (0.40 g, 0.86 mmol). LCMS: Method C, 2.37 min, MS: ES+ 463.3; $^1$H NMR (400 MHz, DMSO-d$_6$) δ ppm 8.38 (s, 1H), 8.05 (s, 1H), 7.86-7.90 (m, 2H), 7.53-7.60 (m, 3H), 7.27 (d, J=8.8 Hz, 2H), 7.13 (s, 1H), 6.90 (d, J=8.8 Hz, 2H), 5.21 (s, 2H), 3.72 (s, 3H), 1.50 (s, 9H).

Step c.

A solution of tert-butyl (5-(3-(1H-imidazol-1-yl)phenyl)thiazol-2-yl)(4-methoxybenzyl)carbamate (0.40 g, 0.86 mmol) in TFA (8 ml) was heated at 80° C. for 3 h. The resulting reaction mixture was concentrated under reduced pressure and saturated NaHCO$_3$ solution (100 ml) was added in to resulting residue. The resulting mixture was extracted with EtOAc (2×100 ml). The combined organic phase was washed with brine solution (75 ml), dried over Na$_2$SO$_4$, filtered and concentrated under reduced pressure. The obtained residue was triturated with diethyl ether (20 ml) yielding 5-(3-(1H-imidazol-1-yl)phenyl)thiazol-2-amine (0.15 g, 0.62 mmol). LCMS: Method F, 5, 2.56 min, MS: ES+ 242.89; $^1$H NMR (400 MHz, DMSO-d$_6$) δ ppm 8.33 (s, 1H), 7.82 (s, 1H), 7.72 (s, 1H), 7.61 (s, 1H), 7.41-7.49 (m, 2H), 7.24-7.34 (m, 3H), 7.11 (s, 1H).

Steps d-f.

The title compound was synthesised from the intermediate above using a procedure similar to that described for steps a-c of Example 8. LCMS: Method E, 2.37 min, MS: ES+ 382.9, $^1$H NMR (400 MHz, DMSO-d$_6$) δ ppm 12.90 (br s, 1H), 8.40 (s, 1H), 8.18 (s, 1H), 7.97 (d, J=1.6 Hz, 1H), 7.89 (s, 1H), 7.54-7.63 (m, 3H), 7.14 (s, 1H), 3.89-4.00 (m, 2H), 3.73-3.78 (m, 1H), 3.58-3.64 (m, 1H), 2.43-2.50 (m, 2H).

Example 26 N-(3-(3-(1H-imidazol-1-yl)phenyl)isoxazol-5-yl)-1-cyano-3-fluoropyrrolidine-3-carboxamide

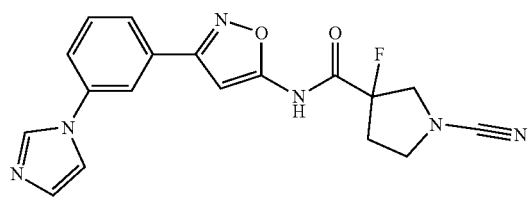 [SMILES: N#CN1CCC(F)(C(=O)Nc2cc(-c3cccc(-n4ccnc4)c3)no2)C1]

Step a.

To a solution of acetonitrile (0.78 ml, 14.851 mmol) in dry THF (20 ml) was added n-BuLi (1.6 M in n-Hexane) (12.38 ml, 19.80 mmol) at −78° C. After 90 min a solution of methyl 3-(1H-imidazol-1-yl)benzoate (CAS Number 335255-85-1) (1.0 g, 4.95 mmol) in dry THF (5 ml) was added slowly to the reaction mixture at −78° C. and the reaction mixture was stirred at −78° C. for 2 h. The resulting reaction mixture was quenched by addition of NH$_4$Cl solution (7-8 ml) and reaction mixture was concentrated under reduced pressure. The resulting residue was purified by flash chromatography (2-4% MeOH in DCM) yielding 3-(3-(1H-imidazol-1-yl) phenyl)-3-oxopropanenitrile (0.8 g, 3.79 mmol). $^1$H NMR (400 MHz, DMSO-d$_6$) δ ppm 8.44 (s, 1H), 8.16 (t, J=1.6 Hz, 1H), 8.00-8.03 (m, 1H), 7.89-7.92 (m, 2H), 7.72 (t, J=8 Hz, 1H), 7.19 (s, 1H), 4.85 (s, 2H).

Step b.

To a solution of 3-(3-(1H-imidazol-1-yl)phenyl)-3-oxopropanenitrile (0.8 g, 3.79 mmol) in ethanol (25 ml) were added hydroxylamine hydrochloride (0.52 g, 7.58 mmol) and NaOAc (0.62 g, 7.58 mmol) at rt. The resulting reaction mixture was heated at reflux for 4 h. The resulting reaction mixture was cooled to rt, poured into water (50 ml) and extracted with EtOAc (3×20 ml). The combined organic phase was washed with brine solution (2×30 ml), dried over Na2SO$_4$, filtered and concentrated under reduced pressure yielding 3-(3-(1H-imidazol-1-yl)phenyl)isoxazol-5-amine (0.8 g, 3.538 mmol). LCMS: Method C, 1.34 min, MS: ES+ 227.35; $^1$H NMR (400 MHz, DMSO-d$_6$) δ ppm 8.36 (s, 1H), 7.94 (t, J=1.6 Hz, 1H), 7.86 (t, J=1.2 Hz, 1H), 7.71-7.74 (m, 2H), 7.58 (t, J=8 Hz, 1H), 7.13 (s, 1H), 6.87 (s, 2H), 5.58 (s, 1H).

Steps c-e.

The title compound was synthesised from the intermediate above using a procedure similar to that described for steps a-c of Example 8. LCMS: Method E, 2.18 min, MS: ES+ 367.0; $^1$H NMR (400 MHz, DMSO-d$_6$) δ ppm 12.33 (s, 1H), 8.43 (s, 1H), 8.15 (t, J=2 Hz 1H), 7.93 (s, 1H), 7.88 (d, J=7.6 Hz, 1H), 7.80-7.83 (m, 1H), 7.65 (t, J=7.6 Hz, 1H), 7.16 (s, 1H), 7.14 (s, 1H), 3.95 (s, 1H), 3.88 (s, 1H), 3.74-3.79 (m, 1H), 3.59-3.65 (m, 1H), 2.44-2.54 (m, 2H).

Example 27 (R)—N-(3-(3-(1H-imidazol-1-yl)phenyl)isoxazol-5-yl)-1-cyano-3-fluoropyrrolidine-3-carboxamide

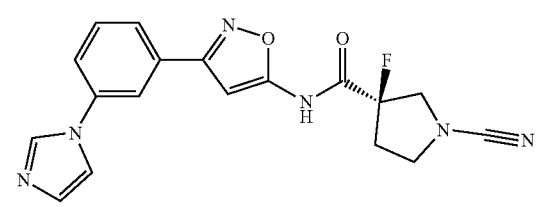 [SMILES: N#CN1CC[C@](F)(C(=O)Nc2cc(-c3cccc(-n4ccnc4)c3)no2)C1]

The title compound was isolated by chiral preparative HPLC of Example 26 to afford the desired enantiomer. LCMS: Method E, 2.18 min, MS: ES+ 367.0; $^1$H NMR (400 MHz, DMSO-d$_6$) δ ppm 12.33 (s, 1H), 8.43 (s, 1H), 8.15 (t, J=2 Hz 1H), 7.93 (s, 1H), 7.88 (d, J=7.6 Hz, 1H), 7.80-7.83 (m, 1H), 7.65 (t, J=7.6 Hz, 1H), 7.16 (s, 1H), 7.14 (s, 1H), 3.95 (s, 1H), 3.88 (s, 1H), 3.74-3.79 (m, 1H), 3.59-3.65 (m, 1H), 2.44-2.54 (m, 2H).

Example 28 N-(6-(1H-pyrazol-5-yl)imidazo[1,2-a]pyridin-2-yl)-1-cyano-3-fluoropyrrolidine-3-carboxamide

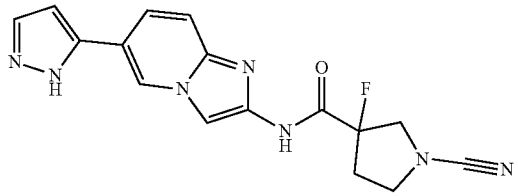 [SMILES: N#CN1CCC(F)(C(=O)Nc2cn3cc(-c4ccn[nH]4)ccc3n2)C1]

Step a.

6-bromoimidazo[1,2-a]pyridin-2-amine and tert-butyl 3-fluoro-3-formylpyrrolidine-1-carboxylate were used in a procedure similar to that described for step a of Example 8 to afford tert-butyl 3-((6-bromoimidazo[1,2-a]pyridin-2-yl)carbamoyl)-3-fluoropyrrolidine-1-carboxylate.

Step b.

tert-butyl 3-((6-bromoimidazo[1,2-a]pyridin-2-yl)carbamoyl)-3-fluoropyrrolidine-1-carboxylate and (1H-pyrazol-5-yl)boronic acid were used in a procedure similar to Example 21 step a to afford tert-butyl 3-((6-(1H-pyrazol-5-yl)imidazo[1,2-a]pyridin-2-yl)carbamoyl)-3-fluoropyrrolidine-1-carboxylate.

Steps c-d.

The title compound was synthesised from the intermediate above using a procedure similar to that described for steps b-c of Example 8. LCMS: Method D, 2.86 min, MS: ES+ 340.5; $^1$H NMR (400 MHz, DMSO-$d_6$) δ ppm 12.98 (s, 1H), 11.13 (s, 1H), 9.05 (s, 1H), 8.21 (s, 1H), 7.84 (s, 1H), 7.75 (d, J=9.2 Hz, 1H), 7.50 (d, J=9.2 Hz, 1H), 6.72 (s, 1H), 3.87-4.05 (m, 1H), 3.81 (s, 1H), 3.72-3.78 (m, 1H), 3.57-3.63 (m, 1H), 2.57-2.61 (m, 1H), 2.38-2.45 (m, 1H).

Example 29 1-cyano-3-fluoro-N-(6-(3-(methylcarbamoyl)phenyl)benzo[d]thiazol-2-yl)pyrrolidine-3-carboxamide

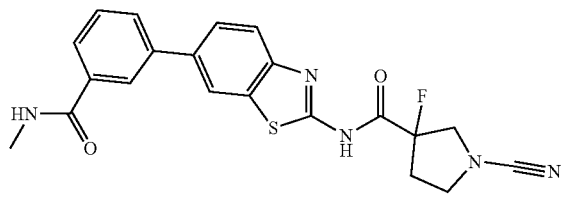 [SMILES: CNC(=O)c1cccc(-c2ccc3nc(NC(=O)C4(F)CCN(C#N)C4)sc3c2)c1]

The title compound was synthesised using a procedure similar to that described for Example 28 using 6-bromobenzo[d]thiazol-2-amine and tert-butyl 3-fluoro-3-formylpyrrolidine-1-carboxylate. LCMS: Method D, 3.64 min, MS: ES+ 424.6; $^1$H NMR (400 MHz, DMSO-$d_6$) δ ppm 12.95 (br, s, 1H), 8.55-8.61 (m, 1H), 8.38 (s, 1H), 8.19 (s, 1H), 7.82-7.89 (m, 4H), 7.57 (t, J=9.6, 1H), 4.00-4.03 (m, 1H), 3.85-3.95 (m, 2H), 3.74-3.78 (m, 1H), 3.58-3.65 (m, 1H), 3.42-3.46 (m, 1H), 2.83 (d, J=4.4 Hz, 3H).

Biological Activity of Compounds of the Invention

Abbreviations

TAMRA carboxytetramethylrhodamine
PCR polymerase chain reaction
PBS phosphate buffered saline
EDTA ethylenediaminetetraacetic acid
Tris 2-amino-2-(hydroxymethyl)-1,3-propanediol
NP-40 Nonidet P-40, octylphenoxypolyethoxyethanol
BSA bovine serum albumin
DMSO dimethyl sulfoxide In Vitro Cezanne 1 Inhibition Assay Expression and Purification of Cezanne 1

The Cezanne 1 construct was PCR amplified and cloned into a pFLAG-CMV-6c vector (Sigma-Aldrich) with an N-terminal FLAG tag. HEK293T cells were transfected with FLAG-Cezanne 1 using TransIT-LT1 transfection reagent (Mirus) according to the manufacturer's instructions. Cells were harvested 48 hours after transfection. Cells were washed once with PBS and scraped in lysis buffer (50 mM Tris, pH 7.5, 150 mM NaCl, 3 mM EDTA, 0.5% NP40, 10% glycerol, 5 mM beta-mercaptoethanol, protease inhibitors (complete mini, Roche) and phosphatase inhibitors (PhosSTOP mini, Roche). Lysates were incubated for 30 min on ice and centrifuged at 4000 rpm for 10 min at 4° C. Soluble supernatant was added to FLAG affinity resin (EZview Red ANTI-FLAG M2 affinity gel, Sigma-Aldrich) equilibrated in low salt buffer (20 mM Tris, pH 7.5, 150 mM NaCl, 0.5 mM EDTA, 5 mM beta-mercaptoethanol) and incubated at 4° C. for 3 hours rotating. The resin was spun at 2000 rpm for 2 min and the supernatant was removed. The resin was washed two times with low salt buffer and one time with high salt buffer (20 mM Tris, pH 7.5, 500 mM NaCl, 0.5 mM EDTA, 5 mM beta-mercaptoethanol, protease inhibitors (complete mini, Roche) and phosphatase inhibitors (PhosSTOP mini, Roche). To elute the bound Cezanne 1, elution buffer (10 mM Tris, pH 7.5, 150 mM NaCl, 0.5 mM EDTA, 10% glycerol, 0.5% NP40, 5 mM beta-mercaptoethanol, 0.15 mg/ml 3× FLAG peptide (Sigma-Aldrich)) was added to the resin and incubated at 4° C. for 2.5 hours while rotating. The resin was centrifuged at 4000 rpm for 30 seconds, and the supernatant containing purified FLAG-Cezanne 1 was removed and stored at −80° C.

Cezanne 1 Biochemical Kinetic Assay

Reactions were performed in duplicate in black 384 well plates (small volume, Greiner 784076) in a final reaction volume of 21 μl. Cezanne 1 was diluted in reaction buffer (40 mM Tris, pH 7.5, 0.005% Tween 20, 0.5 mg/ml BSA, 5 mM—beta-mercaptoethanol) to the equivalent of 0, 0.001, 0.050, 0.01 and 0.05 μl/well. Buffer was optimised for optimal temperature, pH, reducing agent, salts, time of incubation, and detergent. Reactions were initiated by the addition of 50 nM of TAMRA labelled peptide linked to ubiquitin via an iso-peptide bond as fluorescence polarisation substrate. Reactions were incubated at room temperature and read every 2 min for 120 min. Readings were performed on a Pherastar Plus (BMG Labtech). λ Excitation 540 nm; λ Emission 590 nm.

Cezanne 1 Biochemical IC50 Assay

Dilution plates were prepared at 21 times the final concentration (2100 μM for a final concentration of 100 μM) in 50% DMSO in a 96-well polypropylene V-bottom plate (Greiner #651201). A typical 8-point dilution series to be 100, 30, 10, 3, 1, 0.3, 0.1, 0.03 M final. Reactions were performed in duplicate in black 384 well plates (small volume, Greiner 784076) in a final reaction volume of 21 μl. Either 1 μl of 50% DMSO or diluted compound was added to the plate. Cezanne 1 was diluted in reaction buffer (40 mM Tris, pH 7.5, 0.005% Tween 20, 0.5 mg/ml BSA, 5 mM—beta-mercaptoethanol) to the equivalent of 0.005 μl/well and 10 μl of diluted Cezanne 1 was added to the compound. Enzyme and compound were incubated for 30 min at room temp. Reactions were initiated by the addition of 50 nM of TAMRA labelled peptide linked to ubiquitin via an iso-peptide bond as fluorescence polarisation substrate. Reactions were read immediately after addition of substrate and following a 2 hr incubation at room temperature. Readings were performed on a Pherastar Plus (BMG Labtech). λ Excitation 540 nm; λ Emission 590 nm.

Activity of Exemplary Compounds in Cezanne 1 biochemical IC50 assay Ranges:
A<0.1 µM;
0.1<B<1 µM;
1<C<10 µM

| Example | IC50 range |
|---------|------------|
| 1 | C |
| 2 | C |
| 3 | B |
| 4 | C |
| 5 | C |
| 6 | C |
| 7 | C |
| 8 | B |
| 9 | B |
| 10 | B |
| 11 | C |
| 12 | C |
| 13 | A |
| 14 | C |
| 15 | C |
| 16 | C |
| 17 | C |
| 18 | B |
| 19 | B |
| 20 | B |
| 21 | B |
| 22 | B |
| 23 | B |
| 24 | B |
| 25 | B |
| 26 | B |
| 27 | B |
| 28 | B |
| 29 | C |

The invention claimed is:

1. A compound of formula (I):

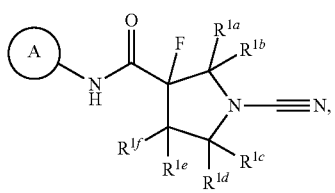

(I)

or a pharmaceutically acceptable salt of said compound, wherein:
$R^{1a}$, $R^{1b}$, $R^{1c}$ and $R^{1d}$ each independently represent hydrogen or $C_1$-$C_6$ alkyl, or $R^{1a}$ is linked to $R^{1b}$ to form a 3 to 6-membered cycloalkyl ring, or $R^{1d}$ is linked to $R^{1c}$ or $R^{1e}$ to form a 3 to 6-membered cycloalkyl ring;
$R^{1e}$ and $R^{1f}$ each independently represent hydrogen, fluorine, cyano, hydroxyl, amino, $C_1$-$C_6$ alkyl, $C_1$-$C_6$ alkoxy or a 5 or 6-membered heteroaryl or aryl ring, or $R^{1e}$ and $R^{1f}$ together form a 3 to 6-membered cycloalkyl ring, or $R^{1e}$ is linked to $R^{1d}$ to form a 3 to 6-membered cycloalkyl ring;
A is a 5 to 10-membered heteroaryl or aryl ring;

wherein ring A is optionally substituted with one to four —$Q^1(R^2)_n$, wherein each occurrence of —$Q^1(R^2)_n$ is the same or different, wherein:
n is 0 or 1;
$Q^1$ represents halogen, cyano, oxo, nitro, —$OR^3$, —$SR^3$, —$NR^3R^4$, —$CONR^3R^4$, —$NR^3COR^4$, —$NR^3CONR^4R^5$, —$COR^3$, —$C(O)OR^3$, —$SO_2R^3$, —$SO_2NR^3R^4$, —$NR^3SO_2R^4$, —$NR^3SO_2NR^4R^5$, —$NR^3C(O)OR^4$, —$C_1$-$C_6$ alkyl, —$C_1$-$C_6$ alkoxy, —$C_2$-$C_6$ alkenyl, a covalent bond, an oxygen atom, a sulphur atom, —SO—, —$SO_2$—, —CO—, —C(O)O—, —$CONR^3$—, —$NR^3$—, —$NR^3CO$—, —$NR^3CONR^4$—, —$SO_2NR^3$—, -$NR^4SO_2$—, —$NR^3SO_2NR^4$—, —$NR^3C(O)O$—, —$NR^3C(O)OR^4$—, $C_1$-$C_6$ alkylene, or —$C_2$-$C_6$ alkenylene;
$R^3$, $R^4$ and $R^5$ each independently represent hydrogen, $C_1$-$C_6$ alkyl or $C_1$-$C_6$ alkylene;
wherein $R^2$ represents a 3 to 10-membered heterocyclyl, heteroaryl, aryl or cycloalkyl ring, which is unsubstituted or substituted with one to four substituents selected from halogen, cyano, oxo, nitro, —$OR^6$, —$SR^6$, —$NR^6R^7$, —$CONR^6R^7$, —$NR^6COR^7$, —$NR^6CONR^7R^8$, —$COR^6$, —$C(O)OR^6$, —$SO_2R^6$, —$SO_2NR^6R^7$, —$NR^6SO_2R^7$, —$NR^6SO_2NR^7R^8$, —$NR^6C(O)OR^7$, $C_1$-$C_6$ alkyl, $C_1$-$C_6$ alkoxy, $C_2$-$C_6$ alkenyl, $C_2$-$C_6$ alkynyl, $Q^2$-$R^6$, —$Q^2$-$NR^6CONR^7R^8$, —$Q^2$-$NR^6R^7$, —$Q^2$-$COR^6$, —$Q^2$-$NR^6COR^7$, —$Q^2$-$NR^6C(O)OR^7$, —$Q^2$-$SO_2R^6$, $Q^2$-$CONR^6R^7$, —$Q^2$-$CO_2R^6$, —$Q^2$-$SO_2NR^6R^7$, —$Q^2$-$NR^6SO_2R^7$ and —$Q^2$-$NR^6SO_2NR^7R^8$;
$Q^2$ represents a covalent bond, an oxygen atom, a sulphur atom, —SO—, —$SO_2$—, —CO—, $C_1$-$C_6$ alkylene, or $C_2$-$C_6$ alkenylene; and
$R^6$, $R^7$, $R^8$ each independently represent hydrogen, $C_1$-$C_6$ alkyl, 3 to 10-membered heterocyclyl ring, 5 to 10-membered heteroaryl ring, 5 to 10-membered aryl ring, or 3 to 10-membered cycloalkyl ring;
wherein said $C_1$-$C_6$ alkyl, $C_1$-$C_6$ alkoxy, $C_2$-$C_6$ alkenyl, $C_2$-$C_6$ alkynyl, $C_1$-$C_6$ alkylene and $C_2$-$C_6$ alkenylene, are each independently optionally substituted with one to four substituents, each independently selected from halogen, hydroxyl, thiol, cyano, amino, nitro, and $SF_5$.

2. The compound according to claim 1, or a pharmaceutically acceptable salt of said compound, wherein $R^{1a}$, $R^{1b}$, $R^{1c}$, $R^{1d}$, $R^{1e}$ and $R^{1f}$ are each hydrogen.

3. The compound according to claim 1, or a pharmaceutically acceptable salt of said compound, wherein the ring of A is a 5 or 6-membered heteroaryl or aryl ring.

4. The compound according to claim 3, or a pharmaceutically acceptable salt of said compound, wherein the ring of A is selected from thiazolyl, imidazolyl, isoxazolyl, pyrazolyl and phenyl.

5. The compound according to claim 4, or a pharmaceutically acceptable salt of said compound, wherein the ring of A is substituted with one to four —$Q^1(R^2)_n$.

6. The compound according to claim 1, or a pharmaceutically acceptable salt of said compound, wherein the ring of A is a 9 or 10-membered bicyclic heteroaryl or aryl ring.

7. The compound according to claim 1, or a pharmaceutically acceptable salt of said compound, wherein the ring of A is selected from benzothiazolyl, imidazopyridinyl and quinolinyl.

8. The compound according to claim 1, or a pharmaceutically acceptable salt of said compound, wherein the ring of A is a nitrogen containing heteroaryl ring.

9. The compound according to claim 1, or a pharmaceutically acceptable salt of said compound, wherein $R^2$ represents an optionally substituted ring selected from pyrazolyl, thiazolyl, phenyl, imidazolyl and indazolyl.

10. The compound according to claim 1, or a pharmaceutically acceptable salt of said compound, wherein $R^2$ is mono-substituted with a substituent selected from cyano, $CONR^6R^7$, $C_1$-$C_3$ alkyl, and imidazolyl, wherein $R^6$ and $R^7$ hydrogen or methyl.

11. The compound according to claim 1, or a pharmaceutically acceptable salt of said compound, wherein when n=1, $Q^1$ is a covalent bond, an oxygen atom or $C_1$-$C_6$ alkyl.

12. The compound according to claim 1, or a pharmaceutically acceptable salt of said compound, wherein when n=0, $Q^1$ is a covalent bond.

13. The compound according to claim 1, or a pharmaceutically acceptable salt of said compound, wherein when n=0, $Q^1$ is halogen or $C_1$-$C_6$ alkyl, wherein $C_1$-$C_6$ alkyl can be further substituted with one or more fluorine.

14. The compound according to claim 1, having the formula (II):

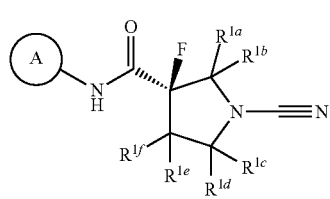

(II)

or a pharmaceutically acceptable salt of said compound.

15. The compound according to claim 1 selected from the group consisting of:
N-(4-chloro-3-(trifluoromethyl)phenyl)-1-cyano-3-fluoropyrrolidine-3-carboxamide;
1-cyano-3-fluoro-N-(4-phenylthiazol-2-yl)pyrrolidine-3-carboxamide;
N-(benzo[d]thiazol-6-yl)-1-cyano-3-fluoropyrrolidine-3-carboxamide;
1-cyano-3-fluoro-N-(quinolin-3-yl)pyrrolidine-3-carboxamide;
1-cyano-3-fluoro-N-(quinolin-6-yl)pyrrolidine-3-carboxamide;
1-cyano-3-fluoro-N-(3-(2-methylthiazol-4-yl)phenyl)pyrrolidine-3-carboxamide;
1-cyano-3-fluoro-N-(3-phenoxyphenyl)pyrrolidine-3-carboxamide;
1-cyano-3-fluoro-N-(5-phenylthiazol-2-yl)pyrrolidine-3-carboxamide;
(R)-1-cyano-3-fluoro-N-(5-phenylthiazol-2-yl)pyrrolidine-3-carboxamide;
1-cyano-3-fluoro-N-(5-phenylisoxazol-3-yl)pyrrolidine-3-carboxamide;
1-cyano-3-fluoro-N-(1-phenyl-1H-imidazol-4-yl)pyrrolidine-3-carboxamide;
(S)-1-cyano-3-fluoro-N-(1-phenyl-1H-pyrazol-4-yl)pyrrolidine-3-carboxamide;
(R)-1-cyano-3-fluoro-N-(1-phenyl-1H-pyrazol-4-yl)pyrrolidine-3-carboxamide;
(R)-1-cyano-N-(1-(4-cyanophenyl)-1H-imidazol-4-yl)-3-fluoropyrrolidine-3-carboxamide;
(R)-N-(1-benzyl-1H-pyrazol-4-yl)-1-cyano-3-fluoropyrrolidine-3-carboxamide;
N-(6-(1H-pyrazol-4-yl)benzo[d]thiazol-2-yl)-1-cyano-3-fluoropyrrolidine-3-carboxamide;
1-cyano-3-fluoro-N-(6-phenylbenzo[d]thiazol-2-yl)pyrrolidine-3-carboxamide;
N-(5-(1H-indazol-4-yl)thiazol-2-yl)-1-cyano-3-fluoropyrrolidine-3-carboxamide;
(R)-N-(5-(1H-indazol-7-yl)thiazol-2-yl)-1-cyano-3-fluoropyrrolidine-3-carboxamide;
1-cyano-3-fluoro-N-(3-phenylisoxazol-5-yl)pyrrolidine-3-carboxamide;
(R)-1-cyano-3-fluoro-N-(3-phenylisoxazol-5-yl)pyrrolidine-3-carboxamide;
N-(5-(3-carbamoylphenyl)thiazol-2-yl)-1-cyano-3-fluoropyrrolidine-3-carboxamide;
1-cyano-3-fluoro-N-(5-(3-(methylcarbamoyl)phenyl)thiazol-2-yl)pyrrolidine-3-carboxamide;
(R)-1-cyano-3-fluoro-N-(5-(3-(methylcarbamoyl)phenyl)thiazol-2-yl)pyrrolidine-3-carboxamide;
N-(5-(3-(1H-imidazol-1-yl)phenyl)thiazol-2-yl)-1-cyano-3-fluoropyrrolidine-3-carboxamide;
N-(3-(3-(1H-imidazol-1-yl)phenyl)isoxazol-5-yl)-1-cyano-3-fluoropyrrolidine-3-carboxamide;
(R)-N-(3-(3-(1H-imidazol-1-yl)phenyl)isoxazol-5-yl)-1-cyano-3-fluoropyrrolidine-3-carboxamide;
N-(6-(1H-pyrazol-5-yl)imidazo[1,2-a]pyridin-2-yl)-1-cyano-3-fluoropyrrolidine-3-carboxamide; and
1-cyano-3-fluoro-N-(6-(3-(methylcarbamoyl)phenyl)benzo[d]thiazol-2-yl)pyrrolidine-3-carboxamide;
or pharmaceutically acceptable salt of said compound.

16. A method for treating cancer linked to Cezanne 1 activity, comprising the step of administering an effective amount of a compound according to claim 1, or a pharmaceutically acceptable salt of said compound, to a patient in need thereof, wherein the patient is afflicted with the cancer.

17. A method according to claim 16, wherein the cancer is selected from breast, ovarian, prostate, lung, kidney, gastric, colon, testicular, head and neck, pancreas, brain, melanoma, bone, cancers of tissue organs, cancers of the blood cells, leukaemia, lymphoma, multiple myeloma, colorectal cancer, non-small cell lung carcinoma.

18. A pharmaceutical composition comprising a compound of formula (I) according to claim 1, or a pharmaceutically acceptable salt of said compound, together with one or more pharmaceutically acceptable excipients.

* * * * *